US009629346B2

(12) United States Patent
Lee et al.

(10) Patent No.: US 9,629,346 B2
(45) Date of Patent: Apr. 25, 2017

(54) ANIMAL MODEL FOR EPILEPSY AND METHOD FOR PRODUCING THE SAME

(71) Applicants: KOREA ADVANCED INSTITUTE OF SCIENCE AND TECHNOLOGY, Daejeon (KR); YONSEI UNIVERSITY, UNIVERSITY—INDUSTRY FOUNDATION (UIF), Seoul (KR)

(72) Inventors: Jeong Ho Lee, Daejeon (KR); Dong Seok Kim, Seoul (KR); Jae Seok Lim, Daejeon (KR); Hoon Chul Kang, Seoul (KR)

(73) Assignees: KOREA ADVANCED INSTITUTE OF SCIENCE AND TECHNOLOGY, Daejeon (KR); YONSEI UNIVERSITY, UNIVERSITY—INDUSTRY FOUNDATION (UIF), Seoul (KR)

(*) Notice: Subject to any disclaimer, the term of this patent is extended or adjusted under 35 U.S.C. 154(b) by 111 days.

(21) Appl. No.: 14/541,252

(22) Filed: Nov. 14, 2014

(65) Prior Publication Data
US 2015/0143560 A1  May 21, 2015

(30) Foreign Application Priority Data

Nov. 15, 2013 (KR) ........................ 10-2013-0139045
Jun. 12, 2014 (KR) ........................ 10-2014-0071588
Aug. 19, 2014 (KR) ........................ 10-2014-0107639

(51) Int. Cl.
| | | |
|---|---|---|
| A01K 67/00 | (2006.01) | |
| A01K 67/033 | (2006.01) | |
| A01K 67/027 | (2006.01) | |
| C12N 9/12 | (2006.01) | |
| C12Q 1/68 | (2006.01) | |

(52) U.S. Cl.
CPC ............ *A01K 67/0275* (2013.01); *C12N 9/12* (2013.01); *C12Q 1/6883* (2013.01); *A01K 2217/05* (2013.01); *A01K 2227/105* (2013.01); *A01K 2267/0356* (2013.01); *C12Q 2600/156* (2013.01); *C12Y 207/11001* (2013.01)

(58) Field of Classification Search
CPC ................................................. A61K 67/0275
See application file for complete search history.

(56) References Cited

FOREIGN PATENT DOCUMENTS

KR   10-1999-0075173     10/1999

OTHER PUBLICATIONS

Griffiths et al, 2000, An Introduction to Genetic Analysis. 7th edition, New York, Freemanand Co. Chapter 15. Gene Mutation, attached pp. 1-3.*
Najm, 2007, Epilepsia, 48(Supple 2):21-32.*
Spindler, Dev Genes Evol, 2010, 220:1-10.*
Wong, 2013, Experimental Neurology, 244:22-26.*
Brian C. Grabiner, Valentina Nardi, Kivanç Birsoy, et al., "A Diverse Array of Cancer-Associated MTOR Mutations Are Hyperactivating and Can Predict Rapamycin Sensitivity", Cancer Discovery. Mar. 14, 2014, vol. 4, pp. 554-563.
Jeong Ho Lee et al., "De novo somatic mutations in components of the PI3K-AKT3-mTOR pathway cause hemimegalencephaly", Nature Genetics. 2012, vol. 44, No. 8, pp. 941-945.
Serine/threonine-protein kinase mTOR[*Homo sapiens*], Genbank NCBI Reference Sequence : NP_004949.1, Sep. 29, 2013.
Predicted : *Homo sapiens* mechanistic target of rapamycin (serine/threonine kinase) (MTOR), transcript variant X1, mRNA, Genbank NCBI Reference Sequence : XM_005263438. 1, Aug. 13, 2013.
John P. A. Loannidis, "Why Most Published Research Findings Are False", Plos Medicine, vol. 2. Issue 8, e124, Aug. 30, 2005.
Robert A. Hegele, "SNP Judgments and Freedom of Association", Arterioscler, Thromb, Vasc. Biol., vol. 22, Issue 7, pp. 1058-1061, Jul. 2002.
H. Juppner, "Functional Properties of the PTH/PTHrP Receptor", Bone, 1995, vol. 17,No. 2, pp. 39S-42S, Aug. 1995.
Lee et al., "De novo somatic mutations in components sof the PI3K-AKT3-mTOR pathway cause hemimegalencephaly", Nature Genetics, vol. 44, No. 8, pp. 941-946, Aug. 2012.

* cited by examiner

*Primary Examiner* — Valarie Bertoglio
(74) *Attorney, Agent, or Firm* — Lex IP Meister, PLLC

(57) ABSTRACT

The present invention relates to a technique for inducing epilepsy and a non-human animal model of epilepsy. More particularly, the present invention relates to a method for inducing epilepsy in an animal, a non-human animal model of epilepsy, and a method for manufacturing the same.

6 Claims, 15 Drawing Sheets
(11 of 15 Drawing Sheet(s) Filed in Color)

ANIMAL MODEL FOR EPILEPSY AND METHOD FOR PRODUCING THE SAME

CROSS-REFERENCE TO RELATED APPLICATIONS

This application claims the benefit of Korean Patent Application No. 10-2013-0139045 on Nov. 15, 2013, 10-2014-0071588 on Jun. 12, 2014, and 10-2014-0107639 on Aug. 19, 2014 with the Korean Intellectual Property Office, the disclosure of which are herein incorporated by reference in its entirety.

BACKGROUND

1. Field

The present invention relates to a technique for inducing epilepsy and a non-human animal model of epilepsy. More particularly, the present invention relates to a method for inducing epilepsy in an animal, a non-human animal model of epilepsy, and a method for manufacturing the same.

2. Description of the Related Art

Epilepsy is a chronic disease to have recurrent seizures which occur as a result of a sudden excessive electrical and synchronized discharge in brain, and is a severe neurological disease accompanied with neurobiological, psychiatric, cognitive, or social impairments.

Epilepsy is one of the most common neurological diseases, affecting approximately 0.5%-1% of the world population. Worldwide, about 45 new epileptic patients per one hundred thousand people are generated every year. In the USA, it is estimated that there are more than 3 million patients with epilepsy, and about 500 new epileptic patients are reported to be generated every day. Further, 70% of cases of epilepsy begin during childhood or adolescence, and in particular, infants are more likely to have epilepsy. The highest incidence and prevalence rates are observed in the first year after the birth of a child, and then drop rapidly. The incidence and prevalence rates rise rapidly again in people over the age of 60, and thus tend to exhibit a U-shaped curve. The prevalence rate of patients who have experienced epileptic seizures in their lives reaches 10-15%.

Epilepsy that fails to respond to anti-epileptic drugs developed until now is called intractable epilepsy, which accounts for approximately 20% cases of epilepsy worldwide.

Malformations of cortical development (MCD) are one of the most common cause of intractable epilepsy. MCDs are a group of disorders characterized by abnormal development of the cerebral cortex due to abnormalities in neuronal migration, differentiation and proliferation, and cause many neurological comorbidities such as developmental delays, mental retardation and cognitive impairments as well as epilepsy. With recent technological advances in brain imaging, such as high-resolution magnetic resonance imaging, etc., diagnosis of malformations of cortical development in patients with intractable epilepsy is rapidly increasing.

Depending on clinical and histopathological features, there are several types of malformations of cortical development. Of them, the most frequent focal cortical dysplasia (FCD), hemimegalencephaly (HME) and tuberous sclerosis complex (TSC) do not respond to existing anti-epileptic drugs, and thus neurosurgical treatment to remove brain lesions is required for controlling epilepsy.

At present, malformations of cortical development are known to be observed in 50% or more of childhood patients with intractable epilepsy that cannot be controlled with medication and thus should be considered for epilepsy surgery. Malformations of cortical development (sporadic MCD) found in childhood patients may occur in one twin of an identical twin pair, and it is also known that sporadic malformations of cortical development occur without specific family history and external stimulation. Understanding of etiology and pathogenetic mechanisms thereof is insufficient.

Accordingly, there is an urgent need to develop disease model for understanding and studying pathology of malformations of cortical development and epilepsy which cause the same.

SUMMARY

An aspect provides a non-human animal model of epilepsy, into which an isolated protein consisting of an amino acid sequence which comprises one or more mutations selected from the group consisting of substitution of tyrosine (Y) for cysteine (C) at position 1483, substitution of arginine (R) for cysteine (C) at position 1483, substitution of lysine (K) for glutamic acid (E) at position 2419, substitution of glycine (G) for glutamic acid (E) at position 2419, substitution of proline (P) for leucine (L) at position 2427, and substitution of glutamine (Q) for leucine (L) at position 2427 in an amino acid sequence of SEQ ID NO. 2; or an isolated gene consisting of a nucleotide sequence which comprises one or more mutations selected from the group consisting of substitution of adenine (A) for guanine (G) at position 4448, substitution of cytosine (C) for thymine (T) at position 4447, substitution of adenine (A) for guanine (G) at position 7255, substitution of guanine (G) for adenine (A) at position 7256, substitution of cytosine (C) for thymine (T) at position 7280, and substitution of adenine (A) for thymine (T) at position 7280 in a nucleotide sequence of SEQ ID NO. 1 is introduced.

Another aspect provides a method for manufacturing the non-human animal model of epilepsy of claim 1, comprising the step of introducing an isolated protein consisting of an amino acid sequence which comprises one or more mutations selected from the group consisting of substitution of tyrosine (Y) for cysteine (C) at position 1483, substitution of arginine (R) for cysteine (C) at position 1483, substitution of lysine (K) for glutamic acid (E) at position 2419, substitution of glycine (G) for glutamic acid (E) at position 2419, substitution of proline (P) for leucine (L) at position 2427, and substitution of glutamine (Q) for leucine (L) at position 2427 in an amino acid sequence of SEQ ID NO. 2; or an isolated gene consisting of a nucleotide sequence which comprises one or more mutations selected from the group consisting of substitution of adenine (A) for guanine (G) at position 4448, substitution of cytosine (C) for thymine (T) at position 4447, substitution of adenine (A) for guanine (G) at position 7255, substitution of guanine (G) for adenine (A) at position 7256, substitution of cytosine (C) for thymine (T) at position 7280, and substitution of adenine (A) for thymine (T) at position 7280 in a nucleotide sequence of SEQ ID NO. 1 into a cell, an embryo or an animal.

Still another aspect provides a method for inducing epilepsy in an animal, comprising the step of introducing an isolated protein consisting of an amino acid sequence which comprises one or more mutations selected from the group consisting of substitution of tyrosine (Y) for cysteine (C) at position 1483, substitution of arginine (R) for cysteine (C) at position 1483, substitution of lysine (K) for glutamic acid (E) at position 2419, substitution of glycine (G) for glutamic acid (E) at position 2419, substitution of proline (P) for leucine (L) at position 2427, and substitution of glutamine (Q) for leucine (L) at position 2427 in an amino acid sequence of SEQ ID NO. 2; or an isolated gene consisting of a nucleotide sequence which comprises one or more mutations selected from the group consisting of substitution of adenine (A) for guanine (G) at position 4448, substitution of cytosine (C) for thymine (T) at position 4447, substitution of adenine (A) for guanine (G) at position 7255, substitution of guanine (G) for adenine (A) at position 7256, substitution of cytosine (C) for thymine (T) at position 7280, and substitution of adenine (A) for thymine (T) at position 7280 in a nucleotide sequence of SEQ ID NO. 1 into a cell, an embryo or an animal.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

In FIG. 8 to FIG. 10, "C1483Y" indicates a brain of embryonic mouse which was electroporated with the plasmid expressing the protein of substitution of tyrosine (Y) for cysteine (C) at position 1483 in an amino acid sequence of SEQ ID NO. 2, "E2419K" indicates a brain of embryonic mouse which was electroporated with the plasmid expressing the protein of substitution of lysine (K) for glutamic acid (E) at position 2419 in an amino acid sequence of SEQ ID NO. 2, and "L2427P" indicates substitution of proline (P) for leucine (L) at position 2427 in an amino acid sequence of SEQ ID NO. 2.

DETAILED DESCRIPTION

In the present invention, each 6 types of mTOR gene mutations which are specifically found in the brain tissues of patients with intractable epilepsy due to malformations of cortical development and mTOR protein mutations thereby were identified (Table 1).

TABLE 1

| | mTOR gene mutations | mTOR protein mutations |
|---|---|---|
| 1 | T4447C | C1483R |
| 2 | G4448A | C1483Y |
| 3 | G7255A | E2419K |
| 4 | A7256G | E2419G |
| 5 | T7280C | L2427P |
| 6 | T7280A | L2427Q |

T4447C indicates a mutation of substitution of cytosine (C) for thymine (T) at position 4447 in nucleotide sequence of mTOR.
G4448A indicates a mutation of substitution of adenine (A) for guanine (G) at position 4448 in nucleotide sequence of mTOR.
G7255A indicates a mutation of substitution of adenine (A) for guanine (G) at position 7255 in nucleotide sequence of mTOR.
A7256G indicates a mutation of substitution of guanine (G) for adenine (A) at position 7256 in nucleotide sequence of mTOR.
T7280C indicates a mutation of substitution of cytosine (C) for thymine (T) at position 7280 in nucleotide sequence of mTOR.
T7280A indicates a mutation of substitution of adenine (A) for thymine (T) at position 7280 in nucleotide sequence of mTOR.
C1483R indicates a mutation of substitution of arginine (R) for cysteine (C) at position 1483 in amino acid sequence of mTOR.
C1483Y indicates a mutation of substitution of tyrosine (Y) for cysteine (C) at position 1483 in amino acid sequence of mTOR.
E2419K indicates a mutation of substitution of lysine (K) for glutamic acid (E) at position 2419 in amino acid sequence of mTOR.
E2419G indicates a mutation of substitution of glycine (G) for glutamic acid (E) at position 2419 in amino acid sequence of mTOR.
L2427P indicates a mutation of substitution of proline (P) for leucine (L) at position 2427 in amino acid sequence of mTOR.
L2427Q indicates a mutation of substitution of glutamine (Q) for leucine (L) at position 2427 in amino acid sequence of mTOR.

Figure 1:
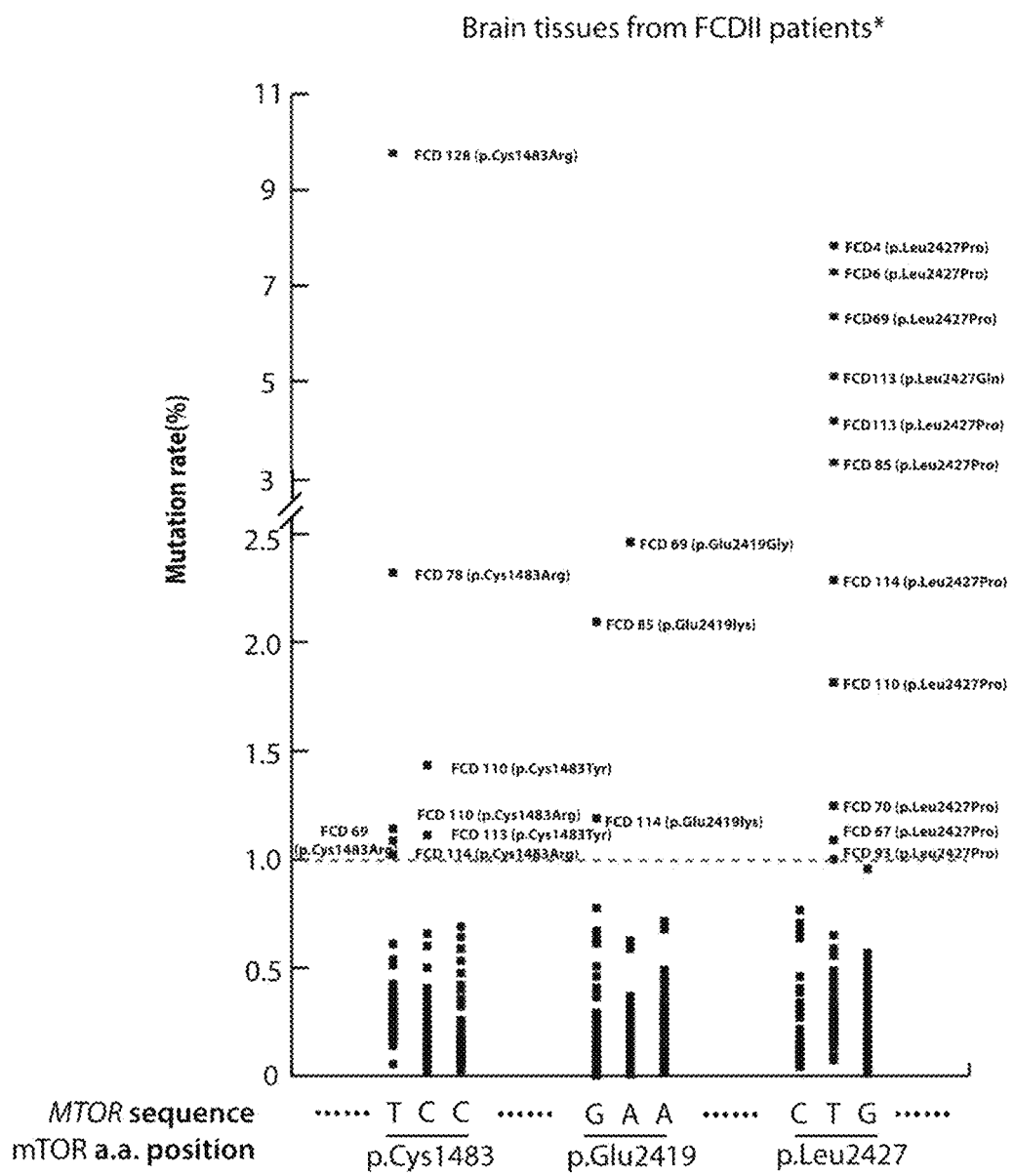
FIG. 1 shows genetic mutations detected in the mTOR target site (containing amino acids, Cys1483, Glu2419, and Leu2427) in the brain tissues of 76 patients with focal cortical dysplasia type IIa (FCDIIa) and focal cortical dysplasia type IIb (FCDIIb), and mutations rates thereof (%).
Figure 2:
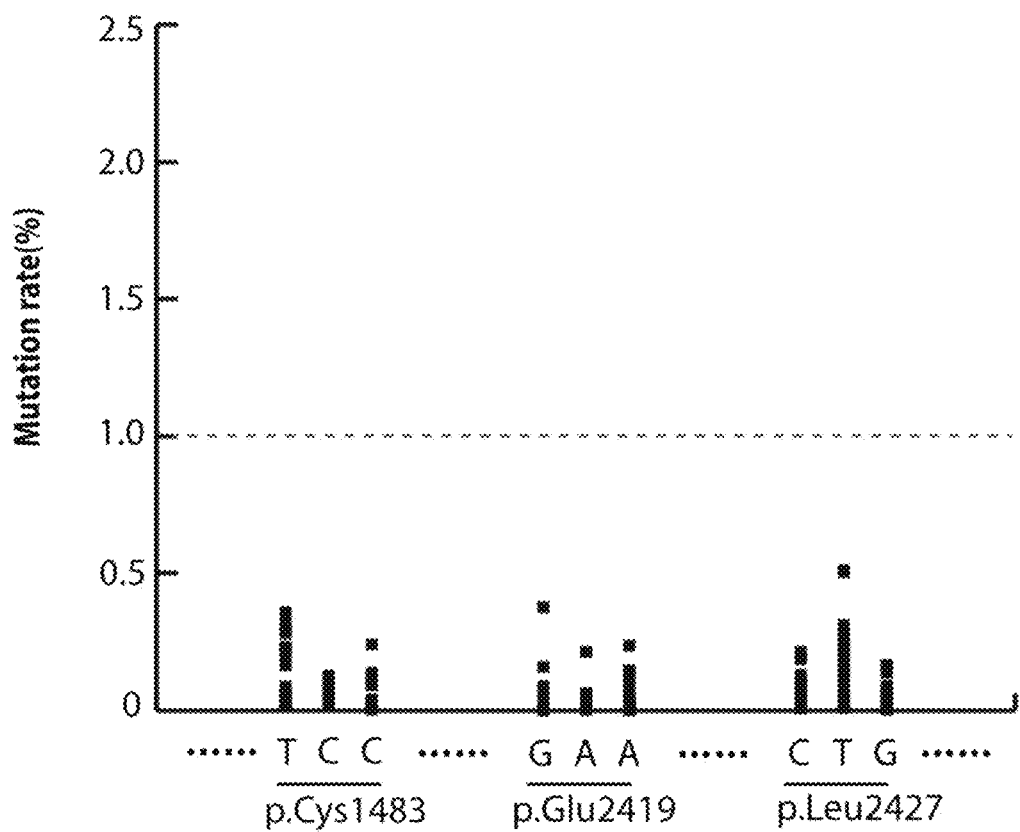
FIG. 2 shows genetic mutations detected in the mTOR target site (containing amino acids, Cys1483, Glu2419, and Leu2427) in the saliva samples of 30 patients with focal cortical dysplasia type IIa and IIb, and mutations rates thereof (%).

Such mTOR gene mutations were not found in the saliva, but in the formalin-fixed, paraffin-embedded brain tissues (FIG. 1 and FIG. 2). It was also found that one or more mutations of the 6 types of genetic mutations were existed in each sample of epilepsy patient, and the genetic mutation rate ranges from 1.03% to 9.77%.

Figure 3:
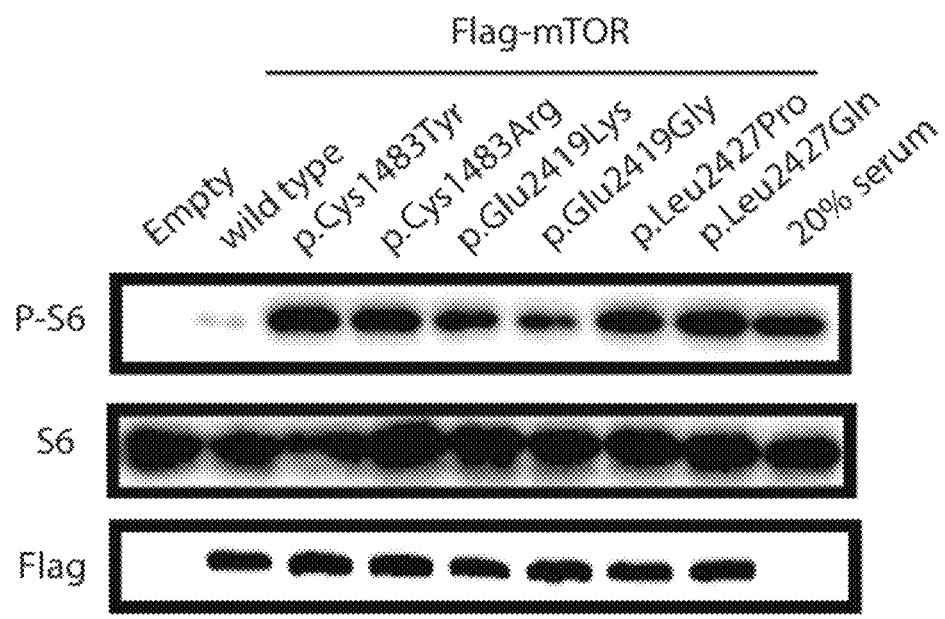
FIG. 3 shows the results of Western blot for analyzing S6 phosphorylation in HEK293T cells which were introduced with the wild-type mTOR protein or each of 6 types of mTOR mutants, in which "Empty" indicates HEK293T cells transfected with empty flag-tagged vector, "P-S6" indicates phosphorylated S6 protein, "S6" indicates S6 protein, "Flag" indicates flag protein, and "20% serum" indicates those exposed to 20% serum for 1 hour and is used as a positive control showing the increased mTOR activity.
Figure 4:
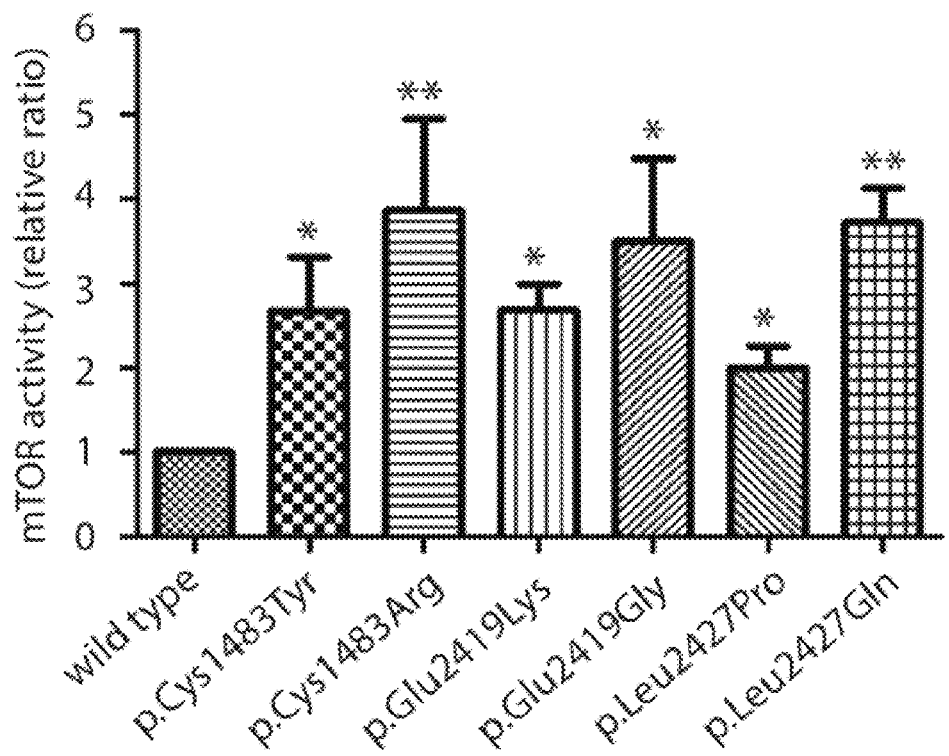
FIG. 4 shows the results of measuring mTOR kinase activity in HEK293T cells which were introduced with the wild-type mTOR protein or each of 6 types of mTOR mutated proteins (*p<0.05 and ***p<0.001, Error bars, s.e.m.).

In the specific Example of the present invention, mTOR mutant construct for expressing one of the 6 types of genetic mutations were prepared and transfected into cells. In the transfected cells, S6 phosphorylation, a well-known biomarker of mTOR activation was increased (FIG. 3), and mTOR kinase activity was also increased (FIG. 4). These results suggest that epilepsy can be caused by the mTOR gene or protein having such mutations.

Figure 5:
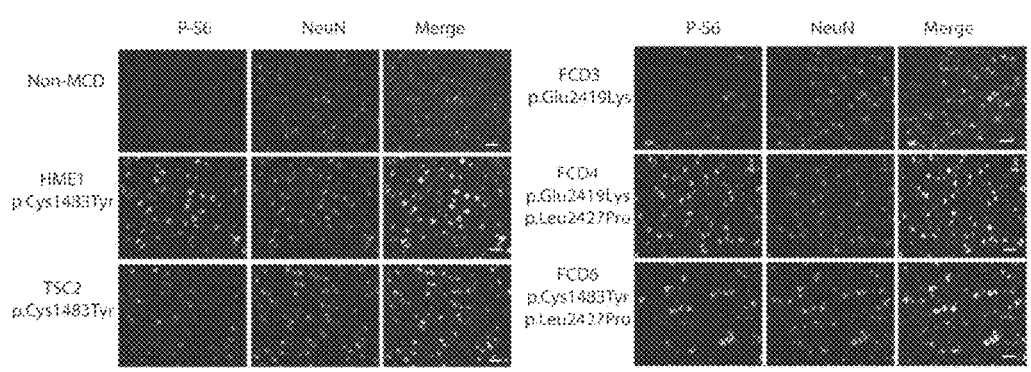
FIG. 5 shows the results of immunohistochemistry in pathological samples of all MCD (Malformations of Cortical Developments) patients identified with mTOR mutations, in which, "Non-MCD" indicates a pathological sample of normal brain, "P-S6" indicates phosphorylated S6 protein, "NeuN" indicates neuronal marker, and "Merge" indicates the merger of P-S6 and NeuN images.
Figure 6:
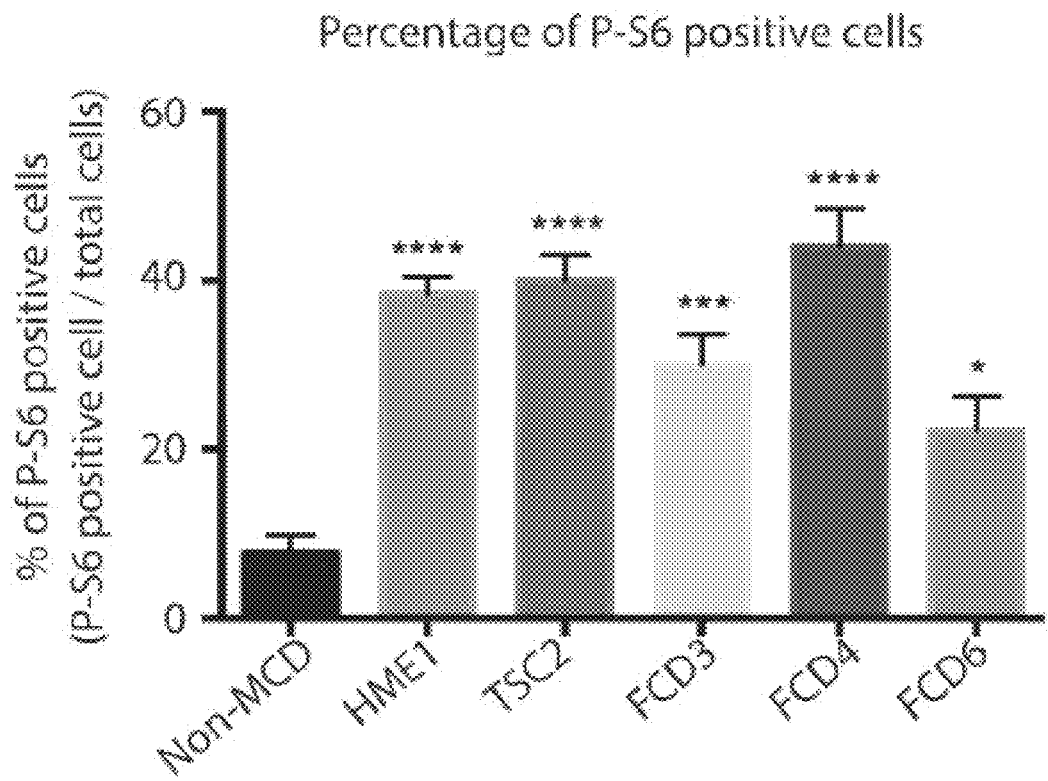
FIG. 6 shows a percentage of cells with positive staining for S6 phosphorylation in 4-5 representative cortical regions. *p<0.05, *P<0.001, *P<0.0001 [relative to Non-MCD samples, one-way ANOVA with Bonferroni posttest]. Error bars, s.e.m. Scale bars, 50 um.
Figure 7:
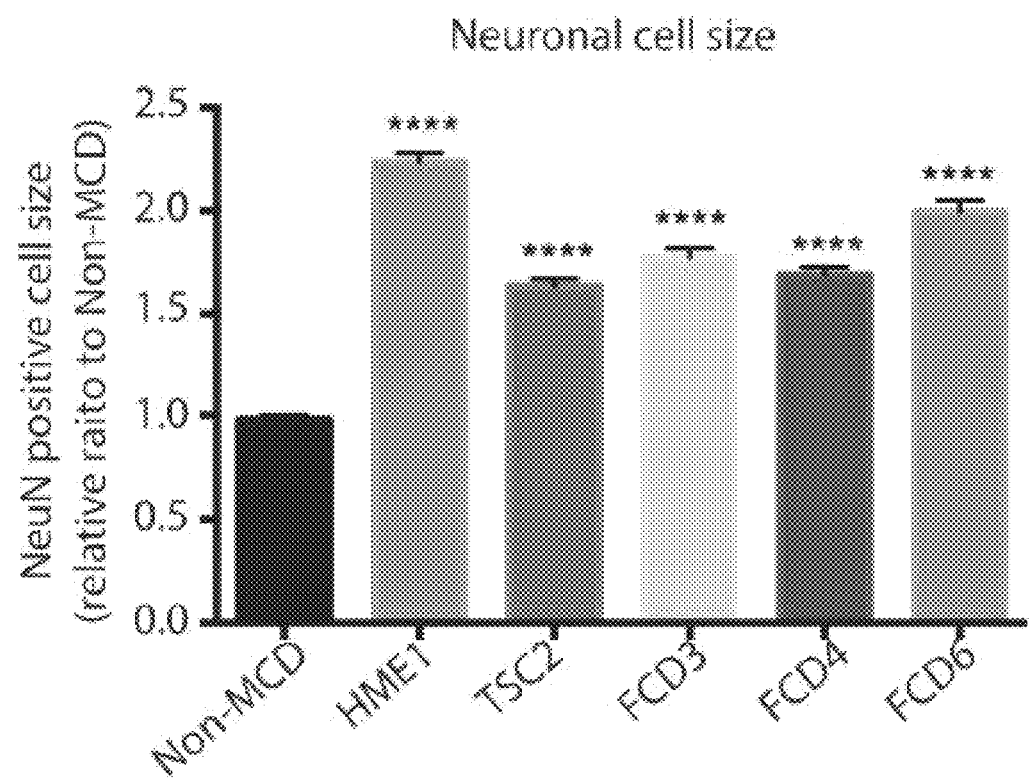
FIG. 7 shows soma size of neurons positive for NeuN, a neuronal marker. The number of counted cell are 994 to 1638 per case. *p<0.05, *P<0.001, *P<0.0001 [relative to Non-MCD samples, one-way ANOVA with Bonferroni posttest]. Error bars, s.e.m. Scale bars, 50 um.

In another Example, as a result of immunohistochemistry in pathological brain sample from patients who had undergone epilepsy surgery (and confirmed the existence of mTOR genetic mutation), an increase of phosphorylated S6 protein as well as a robust increase of soma size of neuronal cell was observed in all pathological sample carrying mTOR mutations (FIG. 5 to FIG. 7).

Figure 9:
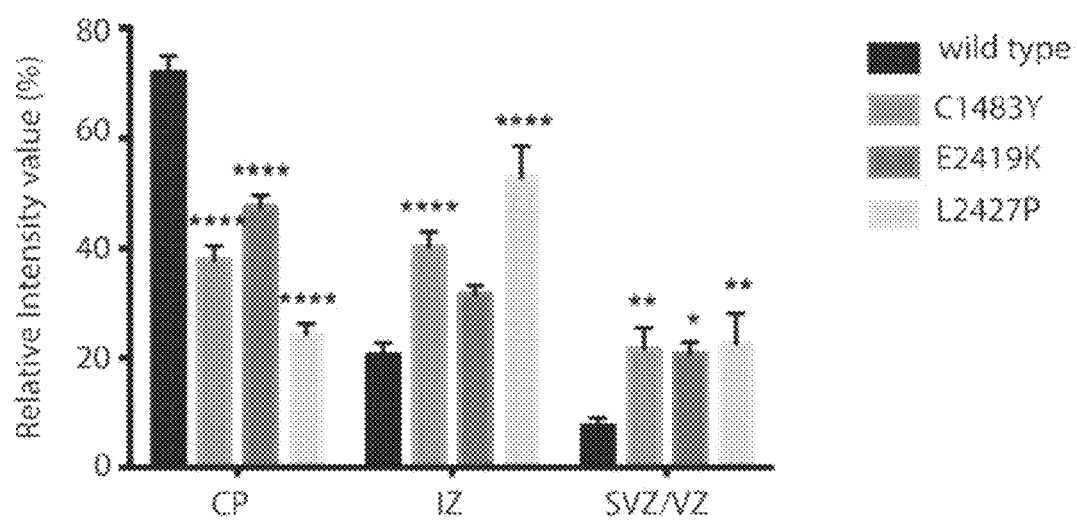
FIG. 9 shows relative fluorescence intensities reflecting the distribution of electroporated cells within the cortex.
Figure 10:
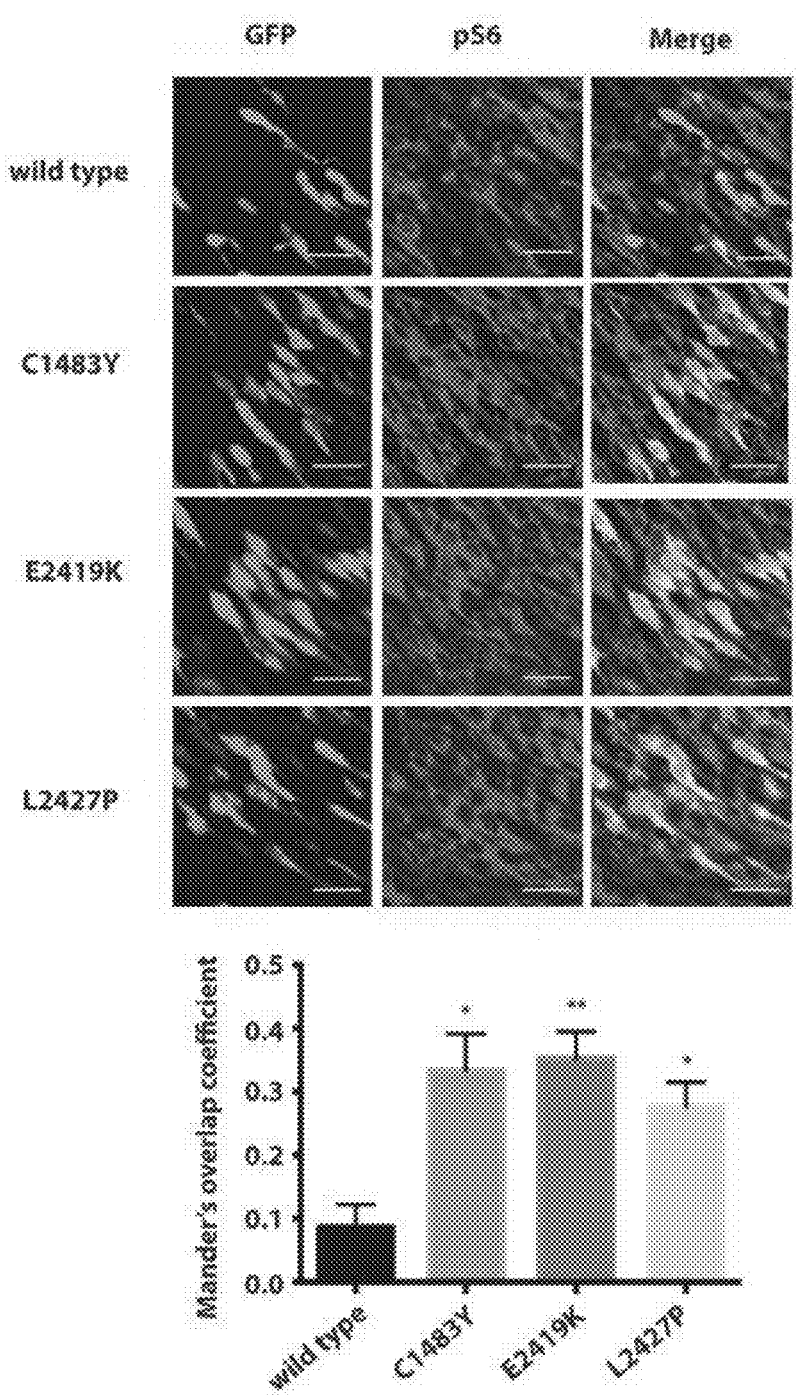
FIG. 10 shows the expressions of GFP and phosphorylated S6 protein of mouse cortex which was electroporated with mTOR mutants according to the invention, in which "pS6" indicates phosphorylated S6 protein, "Merge" indicates the merger of GFP and pS6 images, and "Mander's overlap coefficient" indicates the result of Mander's co-localization analysis.

In addition, a lateral ventricle of each embryonic mouse was injected at E14 with plasmids expressing mTOR C1483Y, mTOR E2419K or mTOR L2427P mutant, and then their brains were harvested after 4d of development (E18). As a result, the disruption of neuronal migration and the increase of phosphorylated S6 protein were found in cerebral cortex in the brain (FIG. 9 and FIG. 10). These results suggest that the mTOR mutants lead to the aberrant activation of mTOR kinase protein and the disruption of normal cortical development.

Figure 11:
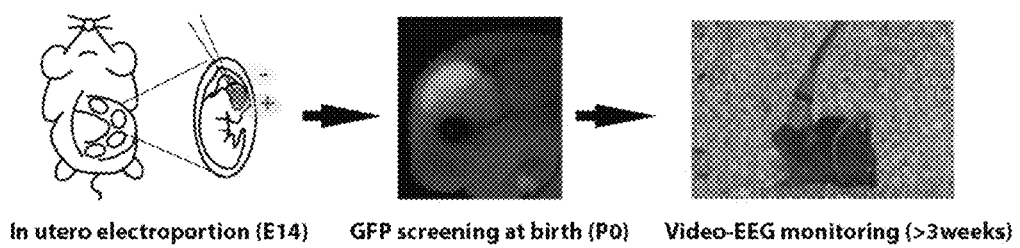
FIG. 11 is a schematic representation showing the procedure for developing embryo which is electroporated with the plasmid containing wild-type mTOR gene or mTOR mutant gene according to the present invention at E14, followed by screening mice expressing fluorescence by flashlight (Electron Microscopy Science, USA), and followed by Video-Electroencephalography (video-EEG) monitoring. In the figure, "In utero electroporation (E14)" indicates a schematic representation of injection of plasmid containing wild-type mTOR gene or mTOR mutant gene according to the present invention at E14, "GFP screening at birth (P0)" indicates a schematic representation of screening mice expressing fluorescence by flashlight (Electron Microscopy Science, USA) after birth, and "Video-EEG monitoring (>3 weeks)" indicates a schematic representation of measuring video-EEG on mouse after weaning (>3 weeks) and being identified as seizure through video monitoring.
Figure 12:
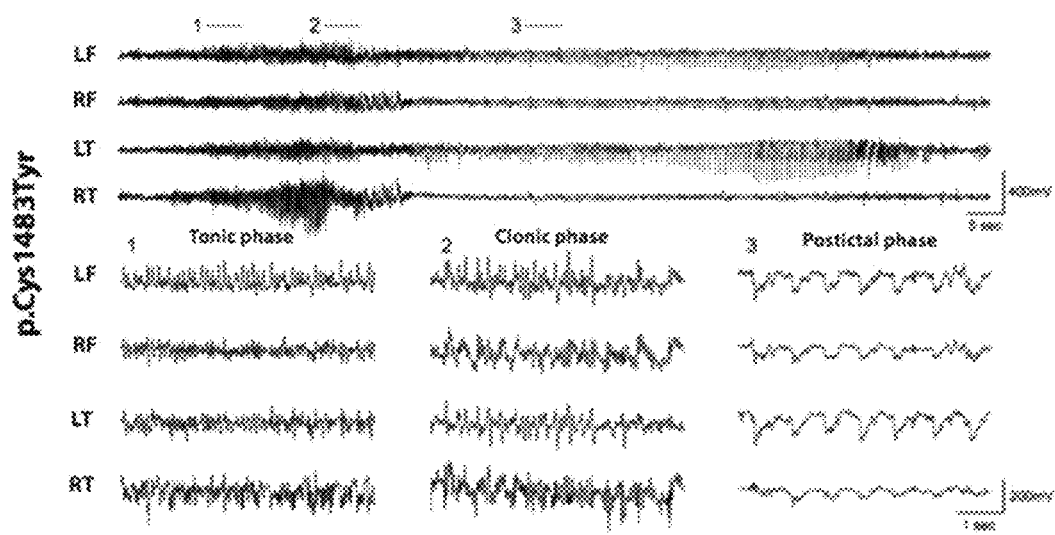
FIG. 12 shows the result of EEG recording from the mouse that was introduced with plasmid (p.Cys1483Tyr) expressing the mTOR mutant protein of substitution of tyrosine (Y) for cysteine (C) at position 1483 in an amino acid sequence of SEQ ID NO. 2.
Figure 13:
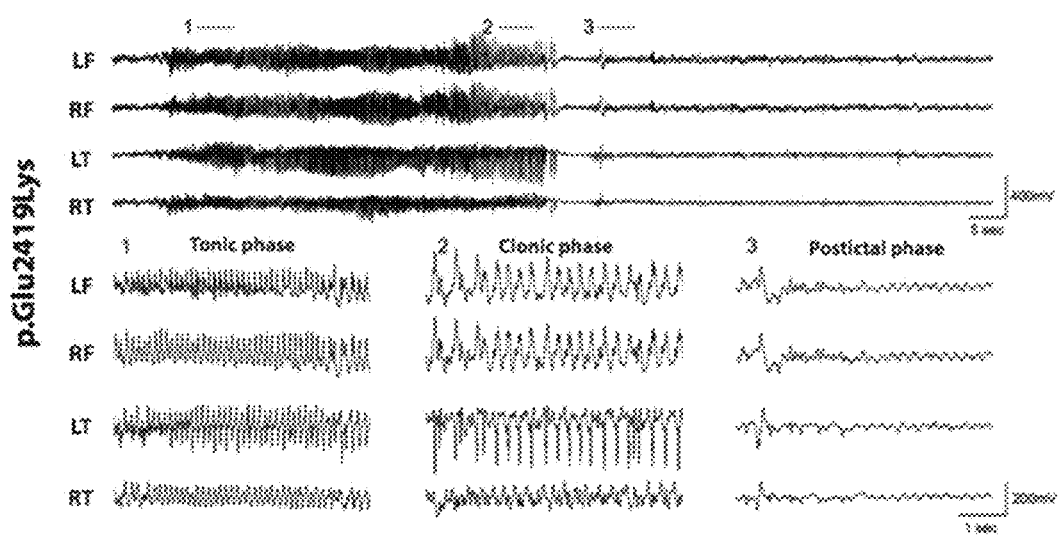
FIG. 13 shows the result of EEG recording from the mouse that was introduced with plasmid (p.Glu2419Lys) expressing the mTOR mutant protein of substitution of lysine (K) for glutamic acid (E) at position 2419 in an amino acid sequence of SEQ ID NO. 2.
Figure 14:
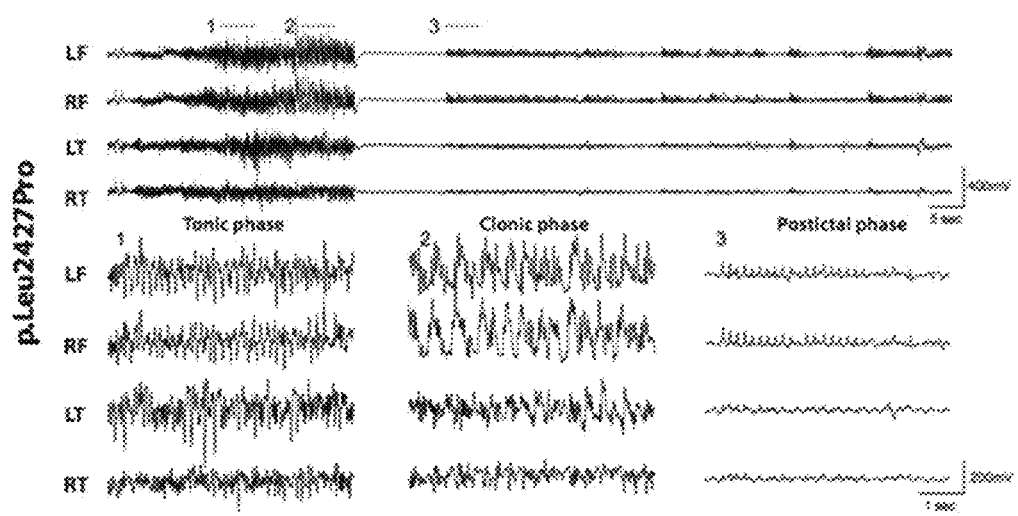
FIG. 14 shows the result of EEG recording from the mouse that was introduced with plasmid (p.Leu2427Pro) expressing the mTOR mutant protein of substitution of proline (P) for leucine (L) at position 2427 in an amino acid sequence of SEQ ID NO. 2.
Figure 15:
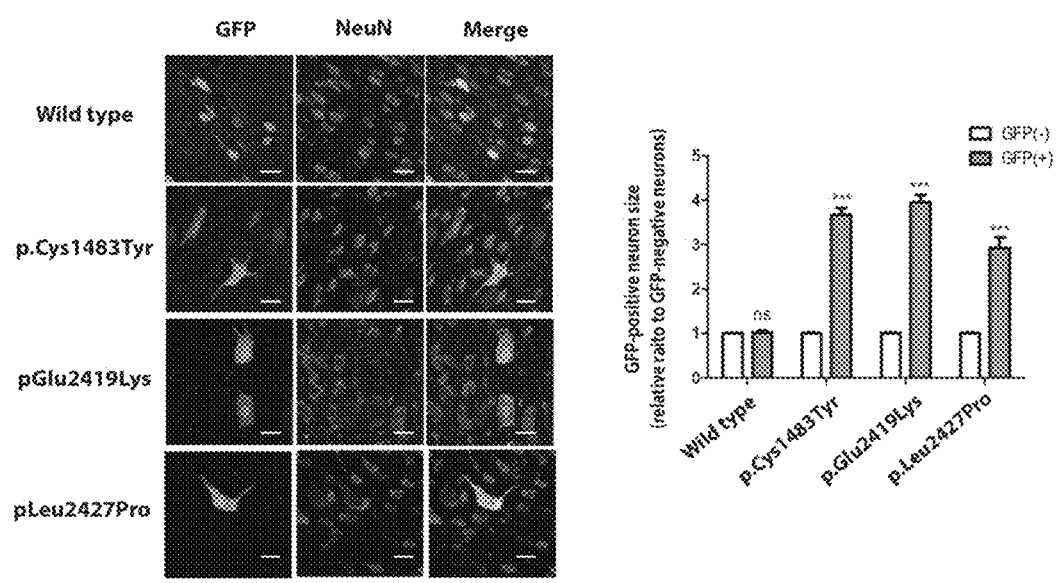
FIG. 15 shows the results of the comparison of cell size between neurons electroporated with plasmid containing mTOR mutant gene according to the present invention and normal neurons.

In another Example, the animal model was prepared by injecting the plasmid expressing mTOR C1483Y, mTOR E2419K or mTOR L2427P mutant into embryonic mice at E14 and inducing the development of the same (FIG. 11). In the result of Video-Electroencephalography (video-EEG), the prepared animal model displayed generalized tonic-clonic seizure, consistent with the symptom of actual patients (FIG. 12 to FIG. 14), and the size of neurons from the animal model was significantly increased than that of normal neurons (FIG. 15).

Therefore, the present invention provides a technique for inducing epilepsy by introducing mTOR mutated gene and/or the mTOR mutated protein encoded by the mutated gene into a cell or an individual, as well as a technique for establishing animal models of epilepsy.

As used herein, the term "epilepsy" refers to a chronic disease to have recurrent seizures which occur as a result of a sudden excessive electrical discharge in a group of nerve cells. In the present invention, the epilepsy includes intractable epilepsy. Further, the epilepsy may be epilepsy which is caused by malformations of cortical development (MCD), and more preferably, intractable epilepsy which is caused by malformations of cortical development. Further, the malformations of cortical development may be focal cortical dysplasia (FCD), hemimegalencephaly (HME) or tuberous sclerosis complex (TSC). Further, in the present invention, the epilepsy may be epilepsy which is accompanied with gene mutations of mTOR gene or amino acid mutations of mTOR protein.

mTOR (mammalian target of rapamycin) protein is the mammalian target protein of rapamycin, and is known as FK506 binding protein 12-rapamycin associated protein 1 (FRAP1). mTOR protein is expressed by FRAP1 gene in humans. mTOR protein is a serine/threonine protein kinase that functionally regulates cell growth, cell proliferation, cell death, cell survival, protein synthesis and transcription, and belongs to the phosphatidylinositol 3-kinase-related kinase protein family. In the present invention, the wild-type mTOR gene sequence is represented by SEQ ID NO. 1, and the mTOR protein sequence is represented by SEQ ID NO. 2.

As used herein, the term "mTOR mutated gene" means that a mutation occurs in the nucleotide sequence of SEQ ID NO. 1 of the wild-type mTOR gene. Preferably, it may be a gene consisting of a nucleotide sequence which includes one or more mutations selected from the group consisting of substitution of C for T at position 4447, substitution of A for G at position 4448, substitution of A for G at position 7255, substitution of G for A at position 7256, substitution of C for T at position 7280, and substitution of A for T at position 7280 in the nucleotide sequence of SEQ ID NO. 1.

As used herein, the term "mTOR mutated protein" means that a mutation occurs in the amino acid sequence of SEQ ID NO. 2 of the wild-type mTOR protein. Preferably, it may be a protein consisting of an amino acid sequence which includes one or more mutations selected from the group consisting of substitution of R for C at position 1483, substitution of Y for C at position 1483, substitution of K for E at position 2419, substitution of G for E at position 2419, substitution of P for L at position 2427, and substitution of Q for L at position 2427 in the amino acid sequence of SEQ ID NO. 2.

Further, the mTOR mutated protein may include an additional mutation within the scope of not altering generally the molecular activity. Amino acid exchanges in proteins and peptides which do not generally alter the molecular activity are known in the art. In some cases, the mTOR mutated protein may be modified by phosphorylation, sulfation, acrylation, glycosylation, methylation, farnesylation or the like.

An aspect provides a non-human animal model of epilepsy, into which
an isolated protein consisting of an amino acid sequence which comprises one or more mutations selected from the group consisting of substitution of tyrosine (Y) for cysteine (C) at position 1483, substitution of arginine (R) for cysteine (C) at position 1483, substitution of lysine (K) for glutamic acid (E) at position 2419, substitution of glycine (G) for glutamic acid (E) at position 2419, substitution of proline (P) for leucine (L) at position 2427, and substitution of glutamine (Q) for leucine (L) at position 2427 in an amino acid sequence of SEQ ID NO. 2; or an isolated gene consisting of a nucleotide sequence which comprises one or more mutations selected from the group consisting of substitution of adenine (A) for guanine (G) at position 4448, substitution of cytosine (C) for thymine (T) at position 4447, substitution of adenine (A) for guanine (G) at position 7255, substitution of guanine (G) for adenine (A) at position 7256, substitution of cytosine (C) for thymine (T) at position 7280, and substitution of adenine (A) for thymine (T) at position 7280 in a nucleotide sequence of SEQ ID NO. 1 is introduced.

Another aspect provides a method for manufacturing the non-human animal model of epilepsy of claim 1, comprising the step of introducing an isolated protein consisting of an amino acid sequence which comprises one or more mutations selected from the group consisting of substitution of tyrosine (Y) for cysteine (C) at position 1483, substitution of arginine (R) for cysteine (C) at position 1483, substitution of lysine (K) for glutamic acid (E) at position 2419, substitution of glycine (G) for glutamic acid (E) at position 2419, substitution of proline (P) for leucine (L) at position 2427, and substitution of glutamine (Q) for leucine (L) at position 2427 in an amino acid sequence of SEQ ID NO. 2; or an isolated gene consisting of a nucleotide sequence which comprises one or more mutations selected from the group consisting of substitution of adenine (A) for guanine (G) at position 4448, substitution of cytosine (C) for thymine (T) at position 4447, substitution of adenine (A) for guanine (G) at position 7255, substitution of guanine (G) for adenine (A) at position 7256, substitution of cytosine (C) for thymine (T) at position 7280, and substitution of adenine (A) for thymine (T) at position 7280 in a nucleotide sequence of SEQ ID NO. 1 into a cell, an embryo or an animal.

Still another aspect provides a method for inducing epilepsy in an animal, comprising the step of introducing an isolated protein consisting of an amino acid sequence which comprises one or more mutations selected from the group consisting of substitution of tyrosine (Y) for cysteine (C) at position 1483, substitution of arginine (R) for cysteine (C) at position 1483, substitution of lysine (K) for glutamic acid (E) at position 2419, substitution of glycine (G) for glutamic acid (E) at position 2419, substitution of proline (P) for leucine (L) at position 2427, and substitution of glutamine (Q) for leucine (L) at position 2427 in an amino acid sequence of SEQ ID NO. 2; or an isolated gene consisting of a nucleotide sequence which comprises one or more mutations selected from the group consisting of substitution of adenine (A) for guanine (G) at position 4448, substitution of cytosine (C) for thymine (T) at position 4447, substitution of adenine (A) for guanine (G) at position 7255, substitution of guanine (G) for adenine (A) at position 7256, substitution of cytosine (C) for thymine (T) at position 7280, and substitution of adenine (A) for thymine (T) at position 7280 in a nucleotide sequence of SEQ ID NO. 1 into a cell, an embryo or an animal.

As used herein, the term "induction" means induction of a change from a normal state into a pathological state. With respect to the objects of the present invention, the induction means that epilepsy is developed from the normal state.

Preferably, epilepsy may be intractable epilepsy caused by malformations of cortical development.

In one embodiment, epilepsy may be induced by introducing the mTOR mutated gene or the mTOR mutated protein into a cell, an embryo or an animal. When the mTOR mutated gene or the mTOR mutated protein is introduced, excessive mTOR activation occurs by mTOR mutations to generate neuronal migration disorders and to dramatically increase S6 protein phosphorylation, leading to epilepsy.

The mTOR protein or the mTOR protein having mutations in the amino acid sequence can be obtained from the natural source by extraction and purification using a method widely known in the art. Otherwise, the mTOR protein having mutations in the amino acid sequence can be chemically synthesized or can be obtained by a recombinant DNA technology.

When the protein is chemically synthesized, it can be obtained by a polypeptide synthetic method widely known in the art. When the recombinant DNA technology is used, a nucleic acid encoding the mTOR protein having mutations in the amino acid sequence is inserted into a suitable expression vector, a host cell is transformed with the vector and then cultured to express the mTOR protein having mutations in the amino acid sequence, and the mTOR protein having mutations in the amino acid sequence is recovered from the host cell. The protein is expressed in the selected host cell, and then a typical biochemical separation technique, for example, treatment by use of a protein precipitant (salting-out), centrifugation, sonication, ultrafiltration, dialysis, a variety of chromatographies such as molecular sieve chromatography (gel filtration), adsorption chromatography, ion-exchange chromatography, or affinity chromatography can be used for separation and purification. Typically, in order to separate a highly pure protein, combinations thereof are used.

The nucleotide sequence encoding the mTOR protein or the mTOR protein having mutations in the amino acid sequence can be isolated from the natural source or prepared by a chemical synthetic method. The nucleic acid having the nucleotide sequence may be single- or double-stranded, and it may be a DNA molecule (genome, cDNA) or an RNA molecule. When the nucleic acid is chemically synthesized, a synthetic method widely known in the art may be used, and examples thereof may include triester, phosphite, phosphoramidite and H-phosphonate methods, PCR and other autoprimer methods, oligonucleotide synthesis on solid supports or the like.

In one embodiment, mTOR mutated gene or the mTOR mutated protein may be introduced into a cell, an embryo or an animal using a recombinant vector.

The vector of the present invention refers to a means for introducing nucleic acid sequences into host cells. The vector includes a plasmid vector, a cosmid vector, a viral vector or the like. Suitable vectors may include a signal sequence or a leader sequence for targeting membranes or secretion as well as expression regulatory elements, such as a promoter, an operator, an initiation codon, a stop codon, a polyadenylation signal and an enhancer, and can be constructed in various forms depending on the purpose thereof. The initiation codon and stop codons are generally considered to be a portion of a nucleotide sequence coding for a target protein, are necessary to be functional in a subject to which a genetic construct has been administered, and must be in frame with the coding sequence. The promoter of the vector may be constitutive or inducible. In addition, expression vectors may include a selectable marker that allows the selection of host cells containing the vector, and replicable expression vectors include a replication origin. The vector may be self-replicable, or may be integrated into the host DNA.

Preferably, the vector may lead to irreversible integration of a gene, which is contained in the vector, into the host genome, and long-term and stable gene expression in the cell.

The mTOR mutated protein or mutated gene of the present invention may be introduced into cells, and preferably, brain cells. In addition, it may be introduced into embryos, and preferably, embryos at the stage of brain formation and development.

The introduction method of the protein or the gene is not particularly limited. For example, a vector may be introduced into cells via a method such as transformation, transfection or transduction. The vector introduced into cells continuously expresses the gene in the cells so as to produce the mTOR protein having mutations in the amino acid sequence.

As used herein, the term "animal model of epilepsy" refers to an animal except human being, in which the modification of characters is induced such that the in vivo activity of mTOR protein is increased compared to the normal cell. The modification may be induced by introducing a vector expressing mTOR protein which comprises variation in its amino acid sequences into the cell. The transgenic animal of epilepsy can be effectively used as an animal model of epilepsy.

As used herein, the term "transgenic animals" means animals having a tumor generated by inducing the modification of characters such that the intracellular PKD2 protein level is increased compared to the normal cell level, and such transgenic animals have a high possibility to be used as tumor animal models.

As used herein, the term "animal model" or "disease model" refers to a non-human animal that has a specific disease similar to a human disease, so that can be used as a subject of study for the purpose of better understanding the pathogenesis and pathophysiology of the disease. Thus, an animal for use as animal model should enable the same effect as in the human beings to be predicted, should be easily produced, should be reproducible, and should show pathogenesis, which is the same as or similar to the pathogenesis of human disease. Thus, a suitable animal model may be an animal, which is a vertebrate mammal, including human being, and, at the same time, has the internal body structures (e.g., internal organs), immune system and body temperature similar to those of human beings, and suffers from disease such as hypertension, cancer, and immune deficiency. Preferably, said animal may be a mammal such as a horse, sheep, pig, goat, camel, antelope, dog, rabbit, mouse, rat, guinea pig and hamster, and more particularly, said animal may be a rodent such as a mouse, rat, guinea pig and hamster. Particularly, mice are most frequently used for the study of human diseases, because they are small prolific animals, are easily managed, show strong resistance to diseases, are genetically uniform, and can produce showing symptoms similar to diseases occurring in human beings.

The animal model of the present invention is a disease model of epilepsy, which is genetically engineered to express mTOR protein that comprises variation in its amino acid sequences. Because the mTOR mutated protein or mutated gene of the present invention can induce epilepsy, the animal model of epilepsy may be easily prepared by introducing the mutant into cells or embryos and inducing the development of the same. Preferably, epilepsy of the present invention may be intractable epilepsy caused by malformations of cortical development.

In one preferred embodiment, the animal model of epilepsy may be prepared by introducing the mTOR mutated protein or mutated gene into an animal embryo and inducing the development of the same. The mTOR mutated protein or mutated gene may be comprised in a vector for introducing into an embryo. A method for introducing the vector into an embryo is not limited in particular. Preferably, the vector may be introduced into an embryo during the period of cerebral cortex formation.

An animal model of epilepsy of the present invention may be effectively used in the study of gene function, molecular mechanism of epilepsy, and development of a novel anti-epileptic drug.

EXAMPLES

One or more embodiments of the present invention will now be described in further detail with reference to the following Examples. However, these examples are for the illustrative purposes only and are not intended to limit the scope of the invention.

Example 1

Identification of Brain Somatic Mutations 1.1. Sample of Epilepsy Patient

Saliva (about 1 ml) and formalin-fixed, paraffin-embedded brain tissue were obtained with consent from 76 patients after surgery for intractable epilepsy due to malformations of cortical development (Pediatric Neurosurgery and Pediatric Neurology, Severance Hospital). Of 76 patients, 51 patients were diagnosed with focal cortical dysplasia type IIa (FCDIIa) and 25 patients were diagnosed with focal cortical dysplasia type IIb (FCDIIb).

1.2. Targeted Re-Sequencing

Genomic DNAs were isolated from the saliva and formalin-fixed, paraffin-embedded brain tissue samples of 76 patients prepared in Example 2.1 using a Qiamp mini DNA kit (Qiagen) and a prepIT-L2P purification kit (DNAgenotek). Then, two pairs of primers having two targets were prepared so that they contained the mTOR targeted codon region (containing amino acids, Cys1483, Glu2419, and Leu2427).

TABLE 2

| Target region | | primer | SEQ ID NO. |
|---|---|---|---|
| Chr1:11174301~ Chr1:11174513 | forward | 5'-TAGGTTACAGGC CTGGATGG-3' | 3 |
| | reverse | 5'-CTTGGCCTCCCA AAATGTTA-3' | 4 |
| Chr1:11217133~ Chr1:11217344 | forward | 5'-TCCAGGCTACCT GGTATGAGA-3' | 5 |
| | reverse | 5'-GCCTTCCTTTCA AATCCAAA-3' | 6 |

Each primer contains a patient-specific index, and one index per one sample of a patient was used. Therefore, the origin of the nucleotide sequence can be determined during analysis of the genetic mutations. PCR of the target site was performed using the primers thus prepared so as to amplify two targeted nucleotide sequences. Then, a DNA library was prepared using a Truseq DNA kit (Illumina) and targeted re-sequencing was performed using a Miseq or Hiseq sequencer (Illumina).

1.3. Identification of Gene Mutations Present in Specific Region of Target Gene

Sequencing information of the target region with 1156~348630× coverage per 1 patient was obtained from the results of Example 1.2. As a tool for analysis of genetic mutations, IGV viewer and in-house python script were used. When the genetic mutation rate was higher than 1%, it was determined as a genetic mutation. FIG. 1 and FIG. 2 illustrate the genetic mutation rates of the target region in the formalin-fixed, paraffin-embedded brain tissue and saliva.

1.4 Identification of Genetic Mutations in Epilepsy Patients

The results of Example 1.3 showed that 6 types of mTOR genetic mutations and 6 types of protein mutations thereby identified by targeted re-sequencing (Table 3).

TABLE 3

| Patients/Sex | Age at Surgery | Pathology | MRI report | Nucleotide changes | Protein changes | % Mutated allele |
|---|---|---|---|---|---|---|
| FCD67/M | 8 yr 10 m | Cortical dyslamination, Dysmorphic neurons, consistent with FCDIIa | Encephalomalacia involving right parietooccipital lobe | 4447T > C<br>7280T > C | 1483C > R<br>2427L > P | 1.21<br>1.09~3.98 |
| FCD69/F | 3 yr 5 m | Cortical dyslamination, Dysmorphic neurons, consistent with FCDIIa | Diffuse cortical dysplasia in the Rt. Frontal lobe | 4447T > C<br>7256A > G<br>7280T > C | 1483C > R<br>2419E > G<br>2427L > P | 1.03<br>2.46<br>1.79~6.35 |
| FCD70/F | 1 yr 8 m | Cortical dyslamination, Dysmorphic neurons, consistent with FCDIIa | Cortical dysplasia in left insular area, frontal lobe side, right frontal lobe area | 7280T > C | 2427L > P | 1.25~3.86 |
| FCD78/M | 12 yr 1 m | Cortical dyslamination, Dysmorphic neurons, consistent with FCDIIa | Dysplastic cortex, Lt. temporal pole | 4447T > C | 1483C > R | 2.05~2.41 |
| FCD85/F | 17 yr 11 m | Cortical dyslamination, Dysmorphic neurons, consistent with FCDIIa | No abnormal signal intensity | 7255G > A<br>7280T > C | 2419E > K<br>2427L > P | 2.09<br>3.31~4.07 |
| FCD93/F | 3 yr 10 m | Cortical dyslamination, Dysmorphic neurons, consistent with FCDIIa | Cortical dysplasia involving right frontoparietal lobe and right posterior temporal lobe | 7280T > C | 2427L > P | 1.00~1.86 |
| FCD110/F | 14 yr 1 m | Cortical dyslamination, Dysmorphic neurons, balloon cells, consistent with FCDIIb | No abnormal signal intensity | 4447T > C<br>4448G > A<br>7280T > C | 1483C > R<br>1483C > Y<br>2427L > P | 1.09~1.14<br>1.44<br>1.81~4.30 |
| FCD113/F | 10 yr | Cortical dyslamination, Dysmorphic neurons, balloon cells, consistent with FCDIIb | Cortical dysplasia involving left temporal lobe and occipital lobe | 4448G > A<br>7280T > A<br>7280T > C | 1483C > Y<br>2427L > Q<br>2427L > P | 1.11<br>2.86~5.11<br>4.17 |
| FCD114/M | 7 yr 10 m | Cortical dyslamination, Dysmorphic neurons, balloon cells, consistent with FCDIIb | Cortical dysplasia, left middle frontal gyrus | 4447T > C<br>7255G > A<br>7280T > C | 1483C > R<br>2419E > K<br>2427L > P | 1.02<br>1.18<br>2.29~3.88 |
| FCD128/F | 4 yr 4 m | Cortical dyslamination, Dysmorphic neurons, balloon cells, consistent with FCDIIb | Cortical dysplasia, right frontal gyrus | 4447T > C | 1483C > R | 6.61~9.77 |

Such mTOR gene mutations were not found in the saliva, but in the formalin-fixed, paraffin-embedded brain tissues (FIG. 1 and FIG. 2). It was also found that the genetic mutation rate ranges from 1.03% to 9.77%.

The genetic mutations identified were found to be substitution of C for T at position 4447, substitution of G for A at position 7256, substitution of A for T at position 7280, substitution of A for G at position 4448, substitution of A for G at position 7255, and substitution of C for T at position 7280 in the nucleotide sequence of SEQ ID NO. 1 of the mTOR gene (nucleotide sequence of wild-type mTOR gene). Such genetic mutations were found to lead to substitution of R for C at position 1483, substitution of G for E at position 2419, substitution of Q for L at position 2427, substitution of Y for C at position 1483, substitution of K for E at position 2419, and substitution of P for L at position 2427 in the amino acid sequence of SEQ ID NO. 2 of the mTOR protein (amino acid sequence of wild-type mTOR protein).

Further, it was found that 6 patients have a substitution of C for T at position 4447 in the nucleotide sequence of SEQ ID NO. 1 of the mTOR gene, 1 patient has a substitution of G for A at position 7256 in the nucleotide sequence of SEQ ID NO. 1, 1 patient has a substitution of A for T at position 7280 in the nucleotide sequence of SEQ ID NO. 1, 2 patients have a substitution of A for G at position 4448 in the nucleotide sequence of SEQ ID NO. 1 of the mTOR gene, 2 patient has a substitution of A for G at position 7255 in the nucleotide sequence of SEQ ID NO. 1, 7 patient has a substitution of C for T at position 7280 in the nucleotide sequence of SEQ ID NO. 1, and 6 patients have one or more mutations of the six genetic substitution mutations, indicating that epilepsy can be caused by one or more genetic mutations.

Further, the mutations in the nucleotide sequence of the mTOR gene resulted in mutations in the amino acid sequence of the mTOR protein, in which 6 patients have a substitution of R for C at position 1483 in the amino acid sequence of SEQ ID NO. 2 of the mTOR protein, 1 patient has a substitution of G for E at position 2419 in the amino acid sequence of SEQ ID NO. 2, 1 patient has a substitution of Q for L at position 2427 in the amino acid sequence of SEQ ID NO. 2, 2 patients have a substitution of Y for C at position 1483 in the amino acid sequence of SEQ ID NO. 2 of the mTOR protein, 2 patient has a substitution of K for E at position 2419 in the amino acid sequence of SEQ ID NO. 2, 7 patient has a substitution of P for L at position 2427 in the amino acid sequence of SEQ ID NO. 2, and 6 patients have one or more mutations of the six amino acid substitution mutations, indicating that epilepsy can be caused by one or more amino acid mutations.

Example 2

Induction of Intractable Epilepsy Using mTOR Mutated Gene 2.1. Induction of mTOR Mutation and Preparation of mTOR Mutant Construct pcDNA3.1 flag-tagged wild-type mTOR construct was provided by Dr. Kun-Liang Guan at the University of California, San Diego. The construct was used together with a QuikChange II site-directed mutagenesis kit (200523, Stratagene, USA) to prepare vectors expressing mTOR mutant (C1483R, E2419G, L2427Q, C1483Y, E2419K or L2427P).

To prepare a pCIG-mTOR mutant-IRES-EGFP vector, MfeI and MluI restriction enzyme sites were first inserted into pCIG2(CAG promoter-MCS-IRES-EGFP) using the following annealing primers [forward primer 5'-AATTC-CAATTGCCCGGGCTTAAGATCGATACGCGTA-3'(SEQ ID NO. 19) and reverse primer 5'-ccggtacgcgtatcgatcttaagc-ccgggcaattgg-3'(SEQ ID NO. 20)) so as to prepare pCIG-C1. Subcloning of the newly inserted MfeI and MluI restriction enzyme sites was carried out using the following primers [hmTOR-MfeI-flag-F;gATcACAATTGTGGCCACCATG-GACTACAAGGACGACGATGACAAGatgc (SEQ ID NO. 21), and hmTOR-MluI-R;tgatcaACGCGTttacca-gaaagggcaccagccaatatagc (SEQ ID NO. 22)] so as to prepare vector expressing wild-type mTOR, namely, pCIG-mTOR wild type-IRES-EGFP, and vectors expressing mTOR mutant (C1483R, E2419G, L2427Q, C1483Y, E2419K or L2427P), namely, pCIG-mTOR mutant-IRES-EGFP vectors. Table 4 indicates primers used for inducing mutation.

TABLE 4

| | primer | SEQ ID NO. |
|---|---|---|
| C1483R | forward 5'-GGCCTCGAGGCGGCGCATGCGGC-3' | 7 |
| | reverse 5'-GCCGCATGCGCCGCCTCGAGGCC-3' | 8 |
| E2419G | forward 5'-GTCATGGCCGTGCTGGGAGCCTTTG TCTATGAC-3' | 9 |
| | reverse 5'-GTCATAGACAAAGGCTCCCAGCACG GCCATGAC-3' | 10 |
| L2427Q | forward 5'-GTCTATGACCCCTTGCAGAACTGGA GGCTGATG-3' | 11 |
| | reverse 5'-CATCAGCCTCCAGTTCTGCAAGGGG TCATAGAC-3' | 12 |
| C1483Y | forward GCCGCATGCGCTACCTCGAGGCC | 13 |
| | reverse GGCCTCGAGGTAGCGCATGCGGC | 14 |
| E2419K | forward GTGTCATGGCCGTGCTGAAAGCCTTTGT CTATGAC | 15 |
| | reverse GTCATAGACAAAGGCTTTCAGCACGGCC ATGACAC | 16 |
| L2427P | forward GTCTATGACCCCTTGCCGAACTGGAGGC TGATG | 17 |
| | reverse CATCAGCCTCCAGTTCGGCAAGGGGTCA TAGAC | 18 |

2.2. Cell Culture, Transfection, and Western Blot

HEK293T cells (thermoscientific) were cultured in DMEM (Dulbecco's Modified Eagle's Medium) containing 10% FBS under the conditions of 37° C. and 5% $CO_2$. The cells were transfected with empty flag-tagged vector, flag-tagged wild-type mTOR vector and flag-tagged mutant mTOR vector using a jetPRIME transfection reagent (Polyplus, France). For 24 hours after transfection, the cells were serum-starved in DMEM containing 0.1% FBS, and cultured in PBS containing 1 mM $MgCl_2$ and $CaCl_2$ under the conditions of 37° C. and 5% $CO_2$ for 1 hour. The cells were lysed in PBS containing 1% Triton X-100, Halt protease, and phosphatase inhibitor cocktail (78440, Thermo Scientific, USA). Proteins were resolved on SDS-PAGE and transferred to a PVDF membrane (Milipore, USA). The membrane was blocked with 3% BSA in TBS containing 0.1% Tween 20 (TBST). Thereafter, the membrane was washed with TBST four times, repeatedly. The membrane was incubated with a 1:1000 dilution of primary antibodies containing anti-phospho-S6-ribosomal protein (5364, Cell Signaling Technology, USA), anti-S6 ribosomal protein (2217, Cell Signaling Technology, USA) and anti-flag M2 (8164, Cell Signaling Technology, USA) in TBST at 4° C. overnight. After incubation, the membrane was washed with TBST four times, repeatedly. Then, the membrane was incubated with a 1/5000 dilution of HRP-linked anti-rabbit or anti-mouse secondary antibodies (7074, Cell Signaling Technology, USA) at room temperature for 2 hours. The membrane was washed with TBST, and immunodetection was performed using an ECL reaction.

The transfected mTOR mutants were a flag-tagged mTOR mutant expressing a protein having a substitution of arginine (R) for cysteine (C) at position 1483 in the amino acid sequence of SEQ ID NO. 2, a flag-tagged mTOR mutant expressing a protein having a substitution of glycine (G) for glutamic acid (E) at position 2419 in the amino acid sequence of SEQ ID NO. 2, and a flag-tagged mTOR mutant expressing a protein having a substitution of glutamine (Q) for leucine (L) at position 2427 in the amino acid sequence of SEQ ID NO. 2. Further, the transfected mTOR mutants were a flag-tagged mTOR mutant expressing a protein having a substitution of tyrosine (Y) for cysteine (C) at position 1483 in the amino acid sequence of SEQ ID NO. 2, a flag-tagged mTOR mutant expressing a protein having a substitution of lysine (K) for glutamic acid (E) at position 2419 in the amino acid sequence of SEQ ID NO. 2, and a flag-tagged mTOR mutant expressing a protein having a substitution of proline (P) for leucine (L) at position 2427 in the amino acid sequence of SEQ ID NO. 2.

As a result, when the mTOR mutants were transfected, mTOR hyperactivation was observed. The hyperactivation was caused by the mTOR mutants, which was confirmed by phosphorylated S6 protein as an indicator of mTOR activation (FIG. 3).

2.3. In Vitro mTOR Kinase Assay

Phosphorylation activity of mTOR was measured using a K-LISA mTOR activity kit (CBA055, Calbiochem, USA) in accordance with the manufacturer's protocol. The transfected cells (HEK293T cell) were lysed in TBS containing 1% Tween 20, Halt protease and phosphatase inhibitor cocktail. 1 mg of the whole lysate was pre-cleared by adding 15 ul of protein G-beads (10004D, Life technologies, USA) and incubated at 4° C. for 15 minutes. Anti-flag antibody was added to the pre-cleared lysate and incubated at 4° C. overnight. 50 ul of 20% slurry of protein G-beads were added and incubated at 4° C. for 90 minutes. The supernatant was carefully discarded. The pelleted beads were washed with 500 ul of lysis buffer four times, repeatedly and washed once with 1× kinase buffer which was contained in the K-LISA mTOR activity kit. The pelleted beads were re-suspended with 50 ul of 2× kinase buffer and 50 ul of mTOR substrate (p70S6K-GST fusion protein) and incubated at 30° C. for 30 minutes. The reaction mixture was incubated in a Glutathione-coated 96-well plate at 30° C. for 30 minutes. Anti-p70S6K-pT389 antibody, HRP antibody-conjugate and TMB substrate were used to detect the phosphorylated substrate. The relative activity was determined by measuring absorbance at 450 nm.

The transfected cells were cells that were transfected with the flag-tagged mTOR mutant vector expressing a protein having a substitution of arginine (R) for cysteine (C) at position 1483 in the amino acid sequence of SEQ ID NO. 2, the flag-tagged mTOR mutant vector expressing a protein having a substitution of glycine (G) for glutamic acid (E) at position 2419 in the amino acid sequence of SEQ ID NO. 2, and the flag-tagged mTOR mutant vector expressing a protein having a substitution of glutamine (Q) for leucine (L) at position 2427 in the amino acid sequence of SEQ ID NO. 2. Further, the transfected cells were cells that were transfected with the flag-tagged mTOR mutant vector expressing a protein having a substitution of tyrosine (Y) for cysteine (C) at position 1483 in the amino acid sequence of SEQ ID NO. 2, the flag-tagged mTOR mutant vector expressing a protein having a substitution of lysine (K) for glutamic acid (E) at position 2419 in the amino acid sequence of SEQ ID NO. 2, and the flag-tagged mTOR mutant vector expressing a protein having a substitution of proline (P) for leucine (L) at position 2427 in the amino acid sequence of SEQ ID NO. 2.

As a result, greatly increased mTOR kinase activity due to six types of the mutants was observed in the cells transfected with the mTOR mutants (FIG. 4), indicating that epilepsy can be caused by the mTOR gene or protein having such mutations.

Example 3

Identification the Activity of mTOR Mutated Gene for Inducing Intractable Epilepsy 3.1. Immunohistochemistry in Pathological Samples Individuals with FCD, TSC, and HME who had undergone epilepsy surgery were identified through Severance Children's Hospital since 2012. Enrolled patients met study entry criteria for FCD, TSC, and HME and underwent the extensive presurgical evaluations including video electroencephalography (EEG) monitoring, high-resolution MRI, and fluorodexoyglucose (FDG)-PET, and subtraction ictal single photon emission computed tomography (SPECT) co-registered to MRI (SISCOM) to localize anatomic lesions. Table 5 shows clinical and molecular data from focal MCD patients carrying mTOR mutations.

TABLE 5

| Patients/Sex | Age at Surgery | Pathology | MRI report | Nucleotide changes | Protein changes |
|---|---|---|---|---|---|
| HME1/M | 5 m | Cortical dyslamination/ Dysmorphic neurons | diffuse cortical dysplasia on Rt/ Thinkened cortex on Rt/ Deformed corpus callosum on Rt | 4448G>A | 1483C>Y |
| TSC2@/F | 3 yr 8 m | Cortical dyslamination/ Dysmorphic neurons/ balloon cells/ abnormal glial cells | Multifocal subcortical tubers/ multiple subependymal nodules | 4448G>A | 1483C>Y |
| FCD3/M | 7 yr 8 m | Cortical dyslamination/ Dysmorphic neurons | No abnormal signal intensity | 7255G>A | 2419E>K |
| FCD4/F | 5 yr 2 m | Cortical dyslamination/ Dysmorphic neurons | mild brain atropy/No abnormal signal intensity | 7255G>A 7280T>C | 2419E>K 2427L>P |
| FCD6/F | 5 yr | Cortical dyslamination/ Dysmorphic neurons | No abnormal signal intensity | 4448G>A 7280T>C | 1483C>Y 2427L>P |

HME: hemimegalencephaly
TSC: Tuberous sclerosis complex
FCD: focal cortical dysplasia
@: This patient also has germline heterozygous 3355C>T (p.1119Q>*).

Non-MCD brain specimen was collected in the operating room from the tumor free margin of an individual with glioblastoma as part of a planned resection, which was pathologically confirmed as normal brain without tumor. Surgical tissue block were fixed in freshly prepared phosphate-buffered(PB) 4% paraformaldehyde for overnight, cryoprotected overnight in 20% buffered sucrose and made gelatin-embedded tissue blocks (7.5% gelatin in 10% sucrose/PB) stored at −80° C. Cryostat-cut section)(10 um thick) were collected and placed on glass slides, blocked in PBS-GT(0.2% gelatin and 0.2% Triton X-100 in PBS) for 1 h at RT and stained with the following antibodies: rabbit antibody to phosphorylated S6 ribosomal protein(Ser240/Ser244) (1:100 dilution; 5364, Cell signaling Technology) and mouse antibody to NeuN(1:100 dilution; MAB377, Millipore). Samples were then washed in PBS and stained with the following secondary antibodies: Alexa Fluor 555-conjugated goat antibody to mouse(1:200 dilution; A21422, Invitrogen), Alexa Fluor 488-conjugated goat antibody to rabbit(1:200 dilution; A11008, Invitrogen). DAPI included in mounting solution (P36931, Life technology) was used for nuclear staining. Images were acquired using a Leica DMI3000 B inverted microscope. The number of cells positive for NeuN was determined using the 10× objective lens; 4~5 fields were acquired per subject within the neuron-rich regions, and >100 cells were scored per region. The number of DAPI-positive cells represents total cell count. Neuronal cell size was measured in NeuN positive cells using automated counting protocol of ImageJ software.

As a result, an increase in the number of cells positive for phosphorylated S6, as well as a robust increase of soma size of neuronal cell was found in all pathological sample carrying mTOR mutations. Therefore, it is concluded that the identified muations are associated with aberrant mTOR activation and dysregulation of neuronal growth (FIG. 5 to FIG. 7).

3.2. In Utero Electroporation and Image Analysis

Timed pregnant mice (E14) were anesthetized with isoflurane (0.4 L/min of oxygen and isoflurane vaporizer gauge 3 during surgery operation). The uterine horn were exposed, and a lateral ventricle of each embryo was injected using pulled glass capillaries with 2 ug/ml of Fast Green (F7252, Sigma, USA) combined with 2-3 ug of mTOR mutant plasmids expressing mTOR C1483Y, mTOR E2419K or mTOR L2427P mutant as indicated in Example 2.2. Plasmids were electroporated on the head of the embryo by discharging 50V with the ECM830 eletroporator(BTX-harvard apparatus) in five electric pulses of 100 ms at 900-ms intervals. Embryonic mice were electroporated at E14, and then their brains were harvested after 4d of development (E18) and fixed in freshly prepared phosphate-buffered 4% paraformaldehyde for overnight, cryoprotected overnight in 30% buffered sucrose and made gelatin-embedded tissue blocks(7.5% gelatin in 10% sucrose/PB) stored at −80° C. Cryostat-cut sections (30 um thick) were collected and placed on glass slides. DAPI included in mounting solution (P36931, Life technology) was used for nuclear staining. Images were acquired using a Leica DMI3000 B inverted microscope or a Zeiss LSM510 confocal microscope. Fluorescence intensities reflecting the distribution of electroporated cells within the cortex were converted into gray values and measured from the ventricular zone (VZ) to cortical plate (CP) using ImageJ software. Manders co-localization analysis was performed using Fiji software.

Figure 8:
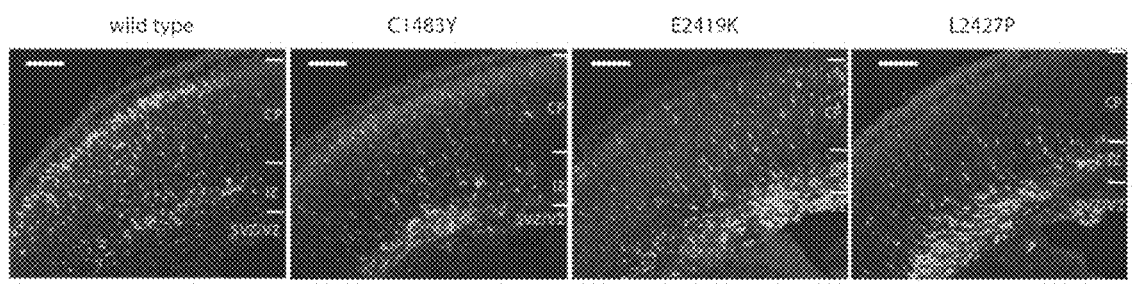
FIG. 8 shows the result of image analysis indicating that in utero electroporation of mTOR mutants disrupts neuronal migration in developing mouse neocortex thereby Malformations of Cortical Developments, in which "CP" indicates cortical plate, "IZ" indicates intermediate zone, "wild type" indicates the image of mouse cortex which was electroporated with wild-type mTOR plasmid, and "Relative intensity value" indicates relative intensities of GFP (green fluorescent protein) in each case.

As a result, the disruption of neuronal migration was found in cerebral cortex in the brain sections of embryos from embryonic day(E) 18 that had been electroporated 4 days previously with GFP expressing mTOR mutant constructs as indicated in Example 2.2, when compared to control group which showed proper neuronal migration (FIG. 8). More particularly, it showed a significant decrease of GFP positive cells in the cortical plate (CP), and an increase in intermediate zone (IZ), subventricular zone (SVZ), and ventricular zone (VZ), thereby indicating the disruption of cortical radial neuronal migration (FIG. 9). In addition, phosphorylated S6 protein was remarkably increased by hyperactivation of mTOR caused by the mTOR mutants in brain section of embryos from embryonic day(E) 18 that had been electroporated at embryonic day(E) 14 (FIG. 10).

These findings suggest that the mTOR mutants cause the aberrant activation of mTOR kinase protein and the disruption of proper cortical developments in vivo.

Example 4

Preparation of Animal Model for Intractable Epilepsy Using mTOR Mutated Gene 4.1. Video-Electroencephalography Monitoring The embryos which had been electroporated with the plasmid containing wild-type mTOR gene or mTOR mutant gene according to the present invention at E14, as indicated in Example 3.2, were borned, then mice expressing fluorescence were screened by flashlight (Electron Microscopy Science, USA) (FIG. 11). After weaning (>3 weeks), the mice were monitored by video monitoring until seizures were observed, and the surgery to implant the electrodes for measuring electroencephalography was performed on mice with seizure.

The electrodes were located on epidural layer. Among five electrodes, two were implanted on frontal lobes (AP+2.8 mm, ML±1.5 mm), two were implanted on temporal lobes (AP−2.4 mm, ML±2.4 mm), and one was implanted on cerebellum region. After 4 days of recovery from the surgery, EEG signals were recorded at from 6 p.m. to 2 a.m. for 2~7 days per mouse. The signals were amplified by amplifier (GRASS model 9 EEG/Polysomnograph, GRASS technologies, USA) and analyzed using pCLAMP program (Molecular Devices, USA).

As a result, the mice which were injected with the plasmid containing mTOR mutant gene according to the present invention displayed generalized tonic-clonic seizure, consistent with the symptom of actual patients (FIG. 12 to FIG. 14), whereas the mice which were injected with the plasmid containing wild-type mTOR gene did not display seizure. The results are summarized in Table 6.

TABLE 6

| Group | No. of GFP + pups | No. of mice with seizure | % |
| --- | --- | --- | --- |
| Wild type | 8 | 0 | 0 |
| p.Cys1483Tyr | 15 | 14 | 93.3 |
| p.Glu2419Lys | 13 | 12 | 92.3 |
| p.Leu2427Pro | 23 | 21 | 91.3 |

4.2. Analysis of Neuronal Size of Born Mice after Electroporation

After Video-Electroencephalography monitoring as indicated in Example 4.1 had done, the mice were perfused with phosphate-buffered (PB) followed by 4% paraformaldehyde using a Masterflex compact peristaltic pump (cole-parmer international, USA), then the brains were harvested. The brains were fixed in freshly prepared phosphate-buffered 4% paraformaldehyde for overnight, cryoprotected overnight in 30% buffered sucrose and made gelatin-embedded tissue blocks(7.5% gelatin in 10% sucrose/PB) stored at −80° C. Cryostat-cut sections (30 um thick) were collected and placed on glass slides, blocked in PBS-GT(0.2% gelatin and 0.2% Triton X-100 in PBS) for 1 h at RT and stained with the following antibodies: mouse antibody to NeuN)(1:500 dilution; MAB377, Millipore). Samples were then washed in PBS and stained with the following secondary antibodies: Alexa Fluor 555-conjugated goat antibody to mouse(1:200 dilution; A21422, Invitrogen). DAPI included in mounting solution (P36931, Life technology) was used for nuclear staining. Images were acquired using a Nikon C2 confocal microscope or a Zeiss LSM510 confocal microscope. The size of neuronal cell was measured using ImageJ software.

As a result, as shown in FIG. 15, the size of neurons from mice which had been electroporated with plasmid containing mTOR mutant gene according to the present invention was significantly increased than that of normal neurons, whereas the size of neurons from mice related to wild-type mTOR gene did not significantly changed. These results are consistent with the aspect of dysmorphic neuron in patients with malformations of cortical development. Accordingly, these results suggest that non-human animal model of epilepsy can be prepared using the mutants provided by the present invention.

What is claimed is:

1. A transgenic non-human mammalian animal model of intractable epilepsy,
   wherein the animal model was made to express a mutant human mTOR protein as a result of the introduction of a mutant human mTOR gene into the developing brain of an embryo during the period of cerebral cortex formation,
   wherein the mutant mTOR protein includes the amino acid sequence of SEQ ID NO. 2 with one or more mutations selected from the group consisting of substitution of tyrosine (Y) for cysteine (C) at position 1483, substitution of arginine (R) for cysteine (C) at position 1483, substitution of lysine (K) for glutamic acid (E) at position 2419, substitution of glycine (G) for glutamic acid (E) at position 2419, substitution of proline (P) for leucine (L) at position 2427, and substitution of glutamine (Q) for leucine (L) at position 2427 of the amino acid sequence,
   wherein the expression of the mutant human mTOR gene resulted in malformation of the cerebral cortex, altered migration, number and size of cortical neurons and spontaneous seizures.

2. The transgenic non-human mammalian animal model of claim 1, wherein the transgenic non-human mammalian animal is a rodent.

3. The transgenic non-human mammalian animal model of claim 1, wherein the brain includes a lateral ventricle.

4. A method for manufacturing the transgenic non-human mammalian animal model of intractable epilepsy of claim 1, comprising the steps of
   introducing a mutant human mTOR gene into the developing brain of a non-human mammalian embryo during the period of cerebral cortex formation; and
   expressing the mutant human mTOR protein in the brain, wherein the mutant human mTOR protein includes the amino acid sequence of SEQ ID NO. 2 with one or more mutations selected from the group consisting of substitution of tyrosine (Y) for cysteine (C) at position 1483, substitution of arginine (R) for cysteine (C) at position 1483, substitution of lysine (K) for glutamic acid (E) at position 2419, substitution of glycine (G) for glutamic acid (E) at position 2419, substitution of proline (P) for leucine (L) at position 2427, and substitution of glutamine (Q) for leucine (L) at position 2427 of the amino acid sequence,
   wherein the expression of the mutant human mTOR gene leads to malformation of the cerebral cortex, altered migration, number and size of cortical neurons and spontaneous seizures.

5. The method of claim 4, wherein the mutant human mTOR gene includes the nucleotide sequence of SEQ ID NO. 1 with one or more mutations selected from the group consisting of substitution of adenine (A) for guanine (G) at position 4448, substitution of cytosine (C) for thymine (T) at position 4447, substitution of adenine (A) for guanine (G) at position 7255, substitution of guanine (G) for adenine (A) at position 7256, substitution of cytosine (C) for thymine (T) at position 7280, and substitution of adenine (A) for thymine (T) at position 7280 of the nucleotide sequence into the embryo.

6. The transgenic non-human animal model of claim 1, wherein the mutant human mTOR protein encoded by the mutant human mTOR gene includes the nucleotide sequence of SEQ ID NO. 1 with one or more mutations selected from the group consisting of substitution of adenine (A) for guanine (G) at position 4448, substitution of cytosine (C) for thymine (T) at position 4447, substitution of adenine (A) for guanine (G) at position 7255, substitution of guanine (G) for adenine (A) at position 7256, substitution of cytosine (C) for thymine (T) at position 7280, and substitution of adenine (A) for thymine (T) at position 7280 of the nucleotide sequence.

* * * * *

```
                        SEQUENCE LISTING

<160> NUMBER OF SEQ ID NOS: 22

<210> SEQ ID NO 1
<211> LENGTH: 7650
<212> TYPE: DNA
<213> ORGANISM: Homo sapiens
<220> FEATURE:
<221> NAME/KEY: gene
<222> LOCATION: (1)..(7650)
<223> OTHER INFORMATION: wild type mTOR

<400> SEQUENCE: 1
atgcttggaa ccggacctgc cgccgccacc accgctgcca ccacatctag caatgtgagc        60
gtcctgcagc agtttgccag tggcctaaag agccggaatg aggaaaccag ggccaaagcc       120
gccaaggagc tccagcacta tgtcaccatg gaactccgag agatgagtca agaggagtct       180
actcgcttct atgaccaact gaaccatcac attttttgaat tggtttccag ctcagatgcc      240
aatgagagga aggtggcat cttggccata gctagcctca taggagtgga aggtgggaat        300
gccacccgaa ttggcagatt tgccaactat cttcggaacc tcctcccctc caatgaccca      360
gttgtcatgg aaatggcatc caaggccatt ggccgtcttg ccatggcagg ggacactttt      420
accgctgagt acgtggaatt tgaggtgaag cgagccctgg aatggctggg tgctgaccgc      480
aatgagggcc ggagacatgc agctgtcctg gttctccgtg agctggccat cagcgtccct      540
accttcttct tccagcaagt gcaacccttc tttgacaaca ttttgtggc cgtgtgggac       600 cccaaacagg ccatccgtga gggagctgta gccgcccttc gtgcctgtct gattctcaca      660
acccagcgtg agccgaagga gatgcagaag cctcagtggt acaggcacac atttgaagaa      720
gcagagaagg gatttgatga gaccttggcc aaagagaagg gcatgaatcg ggatgatcgg      780
atccatggag ccttgttgat ccttaacgag ctggtccgaa tcagcagcat ggagggagag      840
cgtctgagag aagaaatgga agaaatcaca cagcagcagc tggtacacga caagtactgc      900
aaagatctca tgggcttcgg aacaaaacct cgtcacatta cccccttcac cagtttccag      960
gctgtacagc cccagcagtc aaatgccttg gtggggctgc tgggtacag ctctcaccaa      1020 ggcctcatgg gatttggac ctcccccagt ccagctaagt ccaccctggt ggagagccgg      1080
tgttgcagag acttgatgga ggagaaattt gatcaggtgt gccagtgggt gctgaaatgc      1140
aggaatagca agaactcgct gatccaaatg acaatcctta atttgttgcc ccgcttggct      1200
gcattccgac cttctgcctt cacagatacc cagtatctcc aagataccat gaaccatgtc      1260
ctaagctgtg tcaagaagga gaaggaacgt acagcggcct tccaagccct ggggctactt      1320
tctgtggctg tgaggtctga gtttaaggtc tatttgcctc gcgtgctgga catcatccga      1380
gcggccctgc ccccaaagga cttcgcccat aagaggcaga aggcaatgca ggtggatgcc      1440
```

```
acagtcttca cttgcatcag catgctggct cgagcaatgg ggccaggcat ccagcaggat      1500
atcaaggagc tgctggagcc catgctggca gtgggactaa gccctgccct cactgcagtg      1560
ctctacgacc tgagccgtca gattccacag ctaaagaagg acattcaaga tgggctactg      1620
aaaatgctgt ccctggtcct tatgcacaaa ccccttcgcc acccaggcat gcccaagggc      1680
ctggcccatc agctggcctc tcctggcctc acgaccctcc ctgaggccag cgatgtgggc      1740
agcatcactc ttgccctccg aacgcttggc agctttgaat ttgaaggcca ctctctgacc      1800
caatttgttc gccactgtgc ggatcatttc ctgaacagtg agcacaagga gatccgcatg      1860
gaggctgccc gcacctgctc ccgcctgctc acaccctcca tccacctcat cagtggccat      1920
gctcatgtgg ttagccagac cgcagtgcaa gtggtggcag atgtgcttag caaactgctc      1980
gtagttggga taacagatcc tgaccctgac attcgctact gtgtcttggc gtccctggac      2040
gagcgctttg atgcacacct ggcccaggcg agaacttgc aggccttgtt tgtggctctg      2100
aatgaccagg tgtttgagat ccgggagctg gccatctgca ctgtgggccg actcagtagc      2160
atgaaccctg cctttgtcat gccttttcctg cgcaagatgc tcatccagat tttgacagag      2220
ttggagcaca gtgggattgg aagaatcaaa gagcagagtg cccgcatgct ggggcacctg      2280
gtctccaatg cccccccgact catccgcccc tacatggagc ctattctgaa ggcattaatt      2340
ttgaaactga aagatccaga ccctgatcca aacccaggtg tgatcaataa tgtcctggca      2400
acaataggag aattggcaca ggttagtggc ctggaaatga ggaaatgggt tgatgaactt      2460
tttattatca tcatggacat gctccaggat tcctctttgt tggccaaaag gcaggtggct      2520
ctgtggaccc tgggacagtt ggtggccagc actggctatg tagtagagcc ctacaggaag      2580
taccctactt tgcttgaggt gctactgaat tttctgaaga ctgagcagaa ccagggtaca      2640
cgcagagagg ccatccgtgt gttagggctt ttaggggctt tggatcctta caagcacaaa      2700
gtgaacattg gcatgataga ccagtcccgg gatgcctctg ctgtcagcct gtcagaatcc      2760
aagtcaagtc aggattcctc tgactatagc actagtgaaa tgctggtcaa catgggaaac      2820
ttgcctctgg atgagttcta cccagctgtg tccatggtgg ccctgatgcg gatcttccga      2880
gaccagtcac tctctcatca tcacaccatg gttgtccagg ccatcacctt catcttcaag      2940
tccctgggac tcaaatgtgt gcagttcctg ccccaggtca tgcccacgtt ccttaacgtc      3000
attcgagtct gtgatgggggc catccgggaa ttttttgttcc agcagctggg aatgttggtg      3060
tcctttgtga agagccacat cagaccttat atggatgaaa tagtcaccct catgagagaa      3120
ttctgggtca tgaacacctc aattcagagc acgatcattc ttctcattga gcaaattgtg      3180
gtagctcttg ggggtgaatt taagctctac ctgccccagc tgatcccaca catgctgcgt      3240
gtcttcatgc atgacaacag cccaggccgc attgtctcta tcaagttact ggctgcaatc      3300
cagctgtttg gcgccaacct ggatgactac ctgcatttac tgctgcctcc tattgttaag      3360
ttgtttgatg cccctgaagc tccactgcca tctcgaaagg cagcgctaga gactgtggac      3420
cgcctgacgg agtccctgga tttcactgac tatgcctccc ggatcattca ccctattgtt      3480
cgaacactgg accagagccc agaactgcgc tccacagcca tggacacgct gtcttcactt      3540 gttttttcagc tggggaagaa gtaccaaatt ttcattccaa tggtgaataa agttctggtg      3600
cgacaccgaa tcaatcatca gcgctatgat gtgctcatct gcagaattgt caagggatac      3660
acacttgctg atgaagagga ggatcctttg atttaccagc atcggatgct taggagtggc      3720
caaggggatg cattggctag tggaccagtg gaaacaggac ccatgaagaa actgcacgtc      3780
agcaccatca acctccaaaa ggcctggggc gctgccagga gggtctccaa agatgactgg      3840
```

```
ctggaatggc tgagacggct gagcctggag ctgctgaagg actcatcatc gccctccctg   3900
cgctcctgct gggccctggc acaggcctac aacccgatgg ccagggatct cttcaatgct   3960
gcatttgtgt cctgctggtc tgaactgaat gaagatcaac aggatgagct catcagaagc   4020
atcgagttgg ccctcacctc acaagacatc gctgaagtca cacagaccct cttaaacttg   4080
gctgaattca tggaacacag tgacaagggc cccctgccac tgagagatga caatggcatt   4140
gttctgctgg gtgagagagc tgccaagtgc cgagcatatg ccaaagcact acactacaaa   4200
gaactggagt tccagaaagg ccccacccct gccattctag aatctctcat cagcattaat   4260
aataagctac agcagccgga ggcagcggcc ggagtgttag aatatgccat gaaacacttt   4320
ggagagctgg agatccaggc tacctggtat gagaaactgc acgagtggga ggatgccctt   4380
gtggcctatg acaagaaaat ggacaccaac aaggacgacc cagagctgat gctgggccgc   4440
atgcgctgcc tcgaggcctt gggggaatgg ggtcaactcc accagcagtg ctgtgaaaag   4500
tggaccctgg ttaatgatga acccaagcc aagatggccc ggatggctgc tgcagctgca   4560
tggggtttag gtcagtggga cagcatggaa gaatacacct gtatgatccc tcgggacacc   4620
catgatgggg cattttatag agctgtgctg gcactgcatc aggacctctt ctccttggca   4680
caacagtgca ttgacaaggc cagggacctg ctggatgctg aattaactgc gatggcagga   4740
gagagttaca gtcgggcata tggggccatg gtttcttgcc acatgctgtc cgagctggag   4800
gaggttatcc agtacaaact tgtccccgag cgacgagaga tcatccgcca gatctggtgg   4860
gagagactgc agggctgcca gcgtatcgta gaggactggc agaaaatcct tatggtgcgg   4920
tcccttgtgg tcagccctca tgaagacatg agaacctggc tcaagtatgc aagcctgtgc   4980
ggcaagagtg gcaggctggc tcttgctcat aaaactttag tgttgctcct gggagttgat   5040
ccgtctcggc aacttgacca tcctctgcca acagttcacc ctcaggtgac ctatgcctac   5100
atgaaaaaca tgtggaagag tgcccgcaag atcgatgcct tccagcacat gcagcatttt   5160
gtccagacca tgcagcaaca ggcccagcat gccatcgcta ctgaggacca gcagcataag   5220
caggaactgc acaagctcat ggcccgatgc ttcctgaaac ttggagagtg gcagctgaat   5280
ctacagggca tcaatgagag cacaatcccc aaagtgctgc agtactacag cgccgccaca   5340
gagcacgacc gcagctggta caaggcctgg catgcgtggg cagtgatgaa cttcgaagct   5400
gtgctacact caaacatca gaccaagcc cgcgatgaga agaagaaact gcgtcatgcc   5460
agcggggcca acatcaccaa cgccaccact gccgccacca cggccgccac tgccaccacc   5520
actgccagca ccgagggcag caacagtgag agcgaggccg agagcaccga aacagccccc   5580
accccatcgc cgctgcagaa gaaggtcact gaggatctgt ccaaaaccct cctgatgtac   5640
acggtgcctg ccgtccaggg cttcttccgt tccatctcct tgtcacgagg caacaacctc   5700
caggatacac tcagagttct caccttatgg tttgattatg gtcactggcc agatgtcaat   5760
gaggccttag tggaggggt gaaagccatc cagattgata cctggctaca ggttatacct   5820
cagctcattg caagaattga tacgcccaga cccttggtgg acgtctcat tcaccagctt   5880 ctcacagaca ttggtcggta ccaccccag gccctcatct acccactgac agtggcttct   5940
aagtctacca cgacagcccg gcacaatgca gccaacaaga ttctgaagaa catgtgtgag   6000
cacagcaaca ccctggtcca gcaggccatg atggtgagcg aggagctgat ccgagtggcc   6060
atcctctggc atgagatgtg gcatgaaggc ctggaagagg catctcgttt gtactttggg   6120
gaaaggaacg tgaaaggcat gtttgaggtg ctggagccct gcatgctat gatggaacgg   6180
```

```
ggcccccaga ctctgaagga acatcctttt aatcaggcct atggtcgaga tttaatggag    6240
gcccaagagt ggtgcaggaa gtacatgaaa tcagggaatg tcaaggacct cacccaagcc    6300
tgggacctct attatcatgt gttccgacga atctcaaagc agctgcctca gctcacatcc    6360
ttagagctgc aatatgtttc cccaaaactt ctgatgtgcc gggaccttga attggctgtg    6420
ccaggaacat atgaccccaa ccagccaatc attcgcattc agtccatagc accgtctttg    6480
caagtcatca catccaagca gaggcccggg aaattgacac ttatgggcag caacggacat    6540
gagtttgttt tccttctaaa aggccatgaa gatctgcgcc aggatgagcg tgtgatgcag    6600
ctcttcggcc tggttaacac ccttctggcc aatgacccaa catctcttcg gaaaaacctc    6660
agcatccaga gatacgctgt catcccttta tcgaccaact cgggcctcat ggctgggtt     6720 ccccactgtg acacactgca cgccctcatc cgggactaca gggagaagaa gaagatcctt    6780
ctcaacatcg agcatcgcat catgttgcgg atggctccgg actatgacca cttgactctg    6840
atgcagaagg tggaggtgtt tgagcatgcc gtcaataata cagctgggga cgacctggcc    6900
aagctgctgt ggctgaaaag ccccagctcc gaggtgtggt ttgaccgaag aaccaattat    6960
acccgttctt tagcggtcat gtcaatggtt gggtatattt taggcctggg agatagacac    7020
ccatccaacc tgatgctgga ccgtctgagt gggaagatcc tgcacattga ctttgggga    7080 tgctttgagg ttgctatgac ccgagagaag tttccagaga agattccatt tagactaaca    7140
agaatgttga ccaatgctat ggaggttaca ggcctggatg caactacag aatcacatgc    7200 cacacagtga tggaggtgct gcgagagcac aaggacagtg tcatggccgt gctggaagcc    7260
tttgtctatg acccccttgct gaactggagg ctgatggaca caaataccaa aggcaacaag    7320
cgatcccgaa cgaggacgga ttcctactct gctggccagt cagtcgaaat tttggacggt    7380
gtggaacttg gagagccagc ccataagaaa acggggacca cagtgccaga atctattcat    7440
tctttcattg gagacggttt ggtgaaacca gaggccctaa ataagaaagc tatccagatt    7500
attaacaggg ttcgagataa gctcactggt cgggacttct ctcatgatga cacttggat    7560 gttccaacgc aagttgagct gctcatcaaa caagcgacat cccatgaaaa cctctgccag    7620
tgctatattg gctggtgccc tttctggtaa                                      7650
```

<210> SEQ ID NO 2
<211> LENGTH: 2549
<212> TYPE: PRT
<213> ORGANISM: Homo sapiens
<220> FEATURE:
<221> NAME/KEY: PEPTIDE
<222> LOCATION: (1)..(2549)
<223> OTHER INFORMATION: wild type mTOR

<400> SEQUENCE: 2

```
Met Leu Gly Thr Gly Pro Ala Ala Ala Thr Thr Ala Ala Thr Thr Ser
  1               5                  10                  15

Ser Asn Val Ser Val Leu Gln Gln Phe Ala Ser Gly Leu Lys Ser Arg
                 20                  25                  30

Asn Glu Glu Thr Arg Ala Lys Ala Ala Lys Glu Leu Gln His Tyr Val
             35                  40                  45

Thr Met Glu Leu Arg Glu Met Ser Gln Glu Glu Ser Thr Arg Phe Tyr
         50                  55                  60

Asp Gln Leu Asn His His Ile Phe Glu Leu Val Ser Ser Ser Asp Ala
     65                  70                  75                  80

Asn Glu Arg Lys Gly Gly Ile Leu Ala Ile Ala Ser Leu Ile Gly Val
                 85                  90                  95
```

```
              -continued

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510
```

```
Leu Ser Pro Ala Leu Thr Ala Val Leu Tyr Asp Leu Ser Arg Gln Ile
            515                 520                 525

Pro Gln Leu Lys Lys Asp Ile Gln Asp Gly Leu Leu Lys Met Leu Ser
        530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
            610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Ala Asp Val Leu
                645                 650                 655

Ser Lys Leu Leu Val Val Gly Ile Thr Asp Pro Asp Pro Asp Ile Arg
        660                 665                 670

Tyr Cys Val Leu Ala Ser Leu Asp Glu Arg Phe Asp Ala His Leu Ala
    675                 680                 685

Gln Ala Glu Asn Leu Gln Ala Leu Phe Val Ala Leu Asn Asp Gln Val
        690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
```

-continued

```
                930                 935                 940
Glu Phe Tyr Pro Ala Val Ser Met Val Ala Leu Met Arg Ile Phe Arg
945                 950                 955                 960

Asp Gln Ser Leu Ser His His Thr Met Val Gln Ala Ile Thr
                965                 970                 975

Phe Ile Phe Lys Ser Leu Gly Leu Lys Cys Val Gln Phe Leu Pro Gln
                980                 985                 990

Val Met Pro Thr Phe Leu Asn Val Ile Arg Val Cys Asp Gly Ala Ile
                995                 1000                1005

Arg Glu Phe Leu Phe Gln Gln Leu Gly Met Leu Val Ser Phe Val Lys
                1010                1015                1020

Ser His Ile Arg Pro Tyr Met Asp Glu Ile Val Thr Leu Met Arg Glu
1025                1030                1035                1040

Phe Trp Val Met Asn Thr Ser Ile Gln Ser Thr Ile Ile Leu Leu Ile
                1045                1050                1055

Glu Gln Ile Val Val Ala Leu Gly Gly Glu Phe Lys Leu Tyr Leu Pro
                1060                1065                1070

Gln Leu Ile Pro His Met Leu Arg Val Phe Met His Asp Asn Ser Pro
                1075                1080                1085

Gly Arg Ile Val Ser Ile Lys Leu Leu Ala Ala Ile Gln Leu Phe Gly
                1090                1095                1100

Ala Asn Leu Asp Asp Tyr Leu His Leu Leu Pro Pro Ile Val Lys
1105                1110                1115                1120

Leu Phe Asp Ala Pro Glu Ala Pro Leu Pro Ser Arg Lys Ala Ala Leu
                1125                1130                1135

Glu Thr Val Asp Arg Leu Thr Glu Ser Leu Asp Phe Thr Asp Tyr Ala
                1140                1145                1150

Ser Arg Ile Ile His Pro Ile Val Arg Thr Leu Asp Gln Ser Pro Glu
                1155                1160                1165

Leu Arg Ser Thr Ala Met Asp Thr Leu Ser Ser Leu Val Phe Gln Leu
                1170                1175                1180

Gly Lys Lys Tyr Gln Ile Phe Ile Pro Met Val Asn Lys Val Leu Val
1185                1190                1195                1200

Arg His Arg Ile Asn His Gln Arg Tyr Asp Val Leu Ile Cys Arg Ile
                1205                1210                1215

Val Lys Gly Tyr Thr Leu Ala Asp Glu Glu Asp Pro Leu Ile Tyr
                1220                1225                1230

Gln His Arg Met Leu Arg Ser Gly Gln Gly Asp Ala Leu Ala Ser Gly
                1235                1240                1245

Pro Val Glu Thr Gly Pro Met Lys Lys Leu His Val Ser Thr Ile Asn
1250                1255                1260

Leu Gln Lys Ala Trp Gly Ala Ala Arg Val Ser Lys Asp Asp Trp
1265                1270                1275                1280

Leu Glu Trp Leu Arg Arg Leu Ser Leu Glu Leu Leu Lys Asp Ser Ser
                1285                1290                1295

Ser Pro Ser Leu Arg Ser Cys Trp Ala Leu Ala Gln Ala Tyr Asn Pro
                1300                1305                1310

Met Ala Arg Asp Leu Phe Asn Ala Ala Phe Val Ser Cys Trp Ser Glu
                1315                1320                1325

Leu Asn Glu Asp Gln Gln Asp Glu Leu Ile Arg Ser Ile Glu Leu Ala
                1330                1335                1340

Leu Thr Ser Gln Asp Ile Ala Glu Val Thr Gln Thr Leu Leu Asn Leu
1345                1350                1355                1360
```

```
Ala Glu Phe Met Glu His Ser Asp Lys Gly Pro Leu Pro Leu Arg Asp
            1365                1370                1375

Asp Asn Gly Ile Val Leu Leu Gly Glu Arg Ala Ala Lys Cys Arg Ala
            1380                1385                1390

Tyr Ala Lys Ala Leu His Tyr Lys Glu Leu Glu Phe Gln Lys Gly Pro
            1395                1400                1405

Thr Pro Ala Ile Leu Glu Ser Leu Ile Ser Ile Asn Asn Lys Leu Gln
            1410                1415                1420

Gln Pro Glu Ala Ala Ala Gly Val Leu Glu Tyr Ala Met Lys His Phe
1425                1430                1435                1440

Gly Glu Leu Glu Ile Gln Ala Thr Trp Tyr Glu Lys Leu His Glu Trp
            1445                1450                1455

Glu Asp Ala Leu Val Ala Tyr Asp Lys Lys Met Asp Thr Asn Lys Asp
            1460                1465                1470

Asp Pro Glu Leu Met Leu Gly Arg Met Arg Cys Leu Glu Ala Leu Gly
            1475                1480                1485

Glu Trp Gly Gln Leu His Gln Gln Cys Cys Glu Lys Trp Thr Leu Val
            1490                1495                1500

Asn Asp Glu Thr Gln Ala Lys Met Ala Arg Met Ala Ala Ala Ala Ala
1505                1510                1515                1520

Trp Gly Leu Gly Gln Trp Asp Ser Met Glu Glu Tyr Thr Cys Met Ile
            1525                1530                1535

Pro Arg Asp Thr His Asp Gly Ala Phe Tyr Arg Ala Val Leu Ala Leu
            1540                1545                1550

His Gln Asp Leu Phe Ser Leu Ala Gln Gln Cys Ile Asp Lys Ala Arg
            1555                1560                1565

Asp Leu Leu Asp Ala Glu Leu Thr Ala Met Ala Gly Glu Ser Tyr Ser
            1570                1575                1580

Arg Ala Tyr Gly Ala Met Val Ser Cys His Met Leu Ser Glu Leu Glu
1585                1590                1595                1600

Glu Val Ile Gln Tyr Lys Leu Val Pro Glu Arg Arg Glu Ile Ile Arg
            1605                1610                1615

Gln Ile Trp Trp Glu Arg Leu Gln Gly Cys Gln Arg Ile Val Glu Asp
            1620                1625                1630

Trp Gln Lys Ile Leu Met Val Arg Ser Leu Val Val Ser Pro His Glu
            1635                1640                1645

Asp Met Arg Thr Trp Leu Lys Tyr Ala Ser Leu Cys Gly Lys Ser Gly
            1650                1655                1660

Arg Leu Ala Leu Ala His Lys Thr Leu Val Leu Leu Leu Gly Val Asp
1665                1670                1675                1680

Pro Ser Arg Gln Leu Asp His Pro Leu Pro Thr Val His Pro Gln Val
            1685                1690                1695

Thr Tyr Ala Tyr Met Lys Asn Met Trp Lys Ser Ala Arg Lys Ile Asp
            1700                1705                1710

Ala Phe Gln His Met Gln His Phe Val Gln Thr Met Gln Gln Gln Ala
            1715                1720                1725

Gln His Ala Ile Ala Thr Glu Asp Gln Gln His Lys Gln Glu Leu His
            1730                1735                1740

Lys Leu Met Ala Arg Cys Phe Leu Lys Leu Gly Glu Trp Gln Leu Asn
1745                1750                1755                1760

Leu Gln Gly Ile Asn Glu Ser Thr Ile Pro Lys Val Leu Gln Tyr Tyr
            1765                1770                1775
```

```
Ser Ala Ala Thr Glu His Asp Arg Ser Trp Tyr Lys Ala Trp His Ala
            1780                1785                1790

Trp Ala Val Met Asn Phe Glu Ala Val Leu His Tyr Lys His Gln Asn
        1795                1800                1805

Gln Ala Arg Asp Glu Lys Lys Lys Leu Arg His Ala Ser Gly Ala Asn
        1810                1815                1820

Ile Thr Asn Ala Thr Thr Ala Ala Thr Ala Ala Thr Ala Thr Thr
1825                1830                1835                1840

Thr Ala Ser Thr Glu Gly Ser Asn Ser Glu Ser Glu Ala Glu Ser Thr
            1845                1850                1855

Glu Asn Ser Pro Thr Pro Ser Pro Leu Gln Lys Lys Val Thr Glu Asp
        1860                1865                1870

Leu Ser Lys Thr Leu Leu Met Tyr Thr Val Pro Ala Val Gln Gly Phe
        1875                1880                1885

Phe Arg Ser Ile Ser Leu Ser Arg Gly Asn Asn Leu Gln Asp Thr Leu
        1890                1895                1900

Arg Val Leu Thr Leu Trp Phe Asp Tyr Gly His Trp Pro Asp Val Asn
1905                1910                1915                1920

Glu Ala Leu Val Glu Gly Val Lys Ala Ile Gln Ile Asp Thr Trp Leu
        1925                1930                1935

Gln Val Ile Pro Gln Leu Ile Ala Arg Ile Asp Thr Pro Arg Pro Leu
        1940                1945                1950

Val Gly Arg Leu Ile His Gln Leu Leu Thr Asp Ile Gly Arg Tyr His
        1955                1960                1965

Pro Gln Ala Leu Ile Tyr Pro Leu Thr Val Ala Ser Lys Ser Thr Thr
        1970                1975                1980

Thr Ala Arg His Asn Ala Ala Asn Lys Ile Leu Lys Asn Met Cys Glu
1985                1990                1995                2000

His Ser Asn Thr Leu Val Gln Gln Ala Met Met Val Ser Glu Glu Leu
            2005                2010                2015

Ile Arg Val Ala Ile Leu Trp His Glu Met Trp His Glu Gly Leu Glu
        2020                2025                2030

Glu Ala Ser Arg Leu Tyr Phe Gly Glu Arg Asn Val Lys Gly Met Phe
        2035                2040                2045

Glu Val Leu Glu Pro Leu His Ala Met Met Glu Arg Gly Pro Gln Thr
        2050                2055                2060

Leu Lys Glu Thr Ser Phe Asn Gln Ala Tyr Gly Arg Asp Leu Met Glu
2065                2070                2075                2080

Ala Gln Glu Trp Cys Arg Lys Tyr Met Lys Ser Gly Asn Val Lys Asp
        2085                2090                2095

Leu Thr Gln Ala Trp Asp Leu Tyr Tyr His Val Phe Arg Arg Ile Ser
        2100                2105                2110

Lys Gln Leu Pro Gln Leu Thr Ser Leu Glu Leu Gln Tyr Val Ser Pro
        2115                2120                2125

Lys Leu Leu Met Cys Arg Asp Leu Glu Leu Ala Val Pro Gly Thr Tyr
        2130                2135                2140

Asp Pro Asn Gln Pro Ile Ile Arg Ile Gln Ser Ile Ala Pro Ser Leu
2145                2150                2155                2160

Gln Val Ile Thr Ser Lys Gln Arg Pro Arg Lys Leu Thr Leu Met Gly
        2165                2170                2175

Ser Asn Gly His Glu Phe Val Phe Leu Leu Lys Gly His Glu Asp Leu
        2180                2185                2190

Arg Gln Asp Glu Arg Val Met Gln Leu Phe Gly Leu Val Asn Thr Leu
```

```
                  2195                2200                2205
Leu Ala Asn Asp Pro Thr Ser Leu Arg Lys Asn Leu Ser Ile Gln Arg
    2210                2215                2220

Tyr Ala Val Ile Pro Leu Ser Thr Asn Ser Gly Leu Ile Gly Trp Val
2225                2230                2235                2240

Pro His Cys Asp Thr Leu His Ala Leu Ile Arg Asp Tyr Arg Glu Lys
            2245                2250                2255

Lys Lys Ile Leu Leu Asn Ile Glu His Arg Ile Met Leu Arg Met Ala
        2260                2265                2270

Pro Asp Tyr Asp His Leu Thr Leu Met Gln Lys Val Glu Val Phe Glu
    2275                2280                2285

His Ala Val Asn Asn Thr Ala Gly Asp Asp Leu Ala Lys Leu Leu Trp
2290                2295                2300

Leu Lys Ser Pro Ser Ser Glu Val Trp Phe Asp Arg Arg Thr Asn Tyr
2305                2310                2315                2320

Thr Arg Ser Leu Ala Val Met Ser Met Val Gly Tyr Ile Leu Gly Leu
            2325                2330                2335

Gly Asp Arg His Pro Ser Asn Leu Met Leu Asp Arg Leu Ser Gly Lys
        2340                2345                2350

Ile Leu His Ile Asp Phe Gly Asp Cys Phe Glu Val Ala Met Thr Arg
    2355                2360                2365

Glu Lys Phe Pro Glu Lys Ile Pro Phe Arg Leu Thr Arg Met Leu Thr
2370                2375                2380

Asn Ala Met Glu Val Thr Gly Leu Asp Gly Asn Tyr Arg Ile Thr Cys
2385                2390                2395                2400

His Thr Val Met Glu Val Leu Arg Glu His Lys Asp Ser Val Met Ala
            2405                2410                2415

Val Leu Glu Ala Phe Val Tyr Asp Pro Leu Leu Asn Trp Arg Leu Met
        2420                2425                2430

Asp Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu Gly
    2450                2455                2460

Glu Pro Ala His Lys Lys Thr Gly Thr Thr Val Pro Glu Ser Ile His
2465                2470                2475                2480

Ser Phe Ile Gly Asp Gly Leu Val Lys Pro Glu Ala Leu Asn Lys Lys
            2485                2490                2495

Ala Ile Gln Ile Ile Asn Arg Val Arg Asp Lys Leu Thr Gly Arg Asp
        2500                2505                2510

Phe Ser His Asp Asp Thr Leu Asp Val Pro Thr Gln Val Glu Leu Leu
    2515                2520                2525

Ile Lys Gln Ala Thr Ser His Glu Asn Leu Cys Gln Cys Tyr Ile Gly
    2530                2535                2540

Trp Cys Pro Phe Trp
2545

<210> SEQ ID NO 3
<211> LENGTH: 20
<212> TYPE: DNA
<213> ORGANISM: Artificial Sequence
<220> FEATURE:
<223> OTHER INFORMATION: forward primer

<400> SEQUENCE: 3
taggttacag gcctggatgg                                              20
```

```
<210> SEQ ID NO 4
<211> LENGTH: 20
<212> TYPE: DNA
<213> ORGANISM: Artificial Sequence
<220> FEATURE:
<223> OTHER INFORMATION: reverse primer

<400> SEQUENCE: 4
cttggcctcc caaaatgtta                                                   20

<210> SEQ ID NO 5
<211> LENGTH: 21
<212> TYPE: DNA
<213> ORGANISM: Artificial Sequence
<220> FEATURE:
<223> OTHER INFORMATION: forward primer

<400> SEQUENCE: 5
tccaggctac ctggtatgag a                                                 21

<210> SEQ ID NO 6
<211> LENGTH: 20
<212> TYPE: DNA
<213> ORGANISM: Artificial Sequence
<220> FEATURE:
<223> OTHER INFORMATION: reverse primer

<400> SEQUENCE: 6
gccttccttt caaatccaaa                                                   20

<210> SEQ ID NO 7
<211> LENGTH: 23
<212> TYPE: DNA
<213> ORGANISM: Artificial Sequence
<220> FEATURE:
<223> OTHER INFORMATION: forward primer (C1483R)

<400> SEQUENCE: 7
ggcctcgagg cggcgcatgc ggc                                               23

<210> SEQ ID NO 8
<211> LENGTH: 23
<212> TYPE: DNA
<213> ORGANISM: Artificial Sequence
<220> FEATURE:
<223> OTHER INFORMATION: reverse primer (C1483R)

<400> SEQUENCE: 8
gccgcatgcg ccgcctcgag gcc                                               23

<210> SEQ ID NO 9
<211> LENGTH: 33
<212> TYPE: DNA
<213> ORGANISM: Artificial Sequence
<220> FEATURE:
<223> OTHER INFORMATION: forward primer (E2419G)

<400> SEQUENCE: 9
gtcatggccg tgctgggagc ctttgtctat gac                                    33

<210> SEQ ID NO 10
<211> LENGTH: 33
<212> TYPE: DNA
<213> ORGANISM: Artificial Sequence
<220> FEATURE:
```

<223> OTHER INFORMATION: reverse primer (E2419G)

<400> SEQUENCE: 10
gtcatagaca aaggctccca gcacggccat gac					33

<210> SEQ ID NO 11
<211> LENGTH: 33
<212> TYPE: DNA
<213> ORGANISM: Artificial Sequence
<220> FEATURE:
<223> OTHER INFORMATION: forward primer (L2427Q)

<400> SEQUENCE: 11
gtctatgacc ccttgcagaa ctggaggctg atg					33

<210> SEQ ID NO 12
<211> LENGTH: 33
<212> TYPE: DNA
<213> ORGANISM: Artificial Sequence
<220> FEATURE:
<223> OTHER INFORMATION: reverse primer (L2427Q)

<400> SEQUENCE: 12
catcagcctc cagttctgca aggggtcata gac					33

<210> SEQ ID NO 13
<211> LENGTH: 23
<212> TYPE: DNA
<213> ORGANISM: Artificial Sequence
<220> FEATURE:
<223> OTHER INFORMATION: forward primer (C1483Y)

<400> SEQUENCE: 13
gccgcatgcg ctacctcgag gcc					23

<210> SEQ ID NO 14
<211> LENGTH: 23
<212> TYPE: DNA
<213> ORGANISM: Artificial Sequence
<220> FEATURE:
<223> OTHER INFORMATION: reverse primer (C1483Y)

<400> SEQUENCE: 14
ggcctcgagg tagcgcatgc ggc					23

<210> SEQ ID NO 15
<211> LENGTH: 35
<212> TYPE: DNA
<213> ORGANISM: Artificial Sequence
<220> FEATURE:
<223> OTHER INFORMATION: forward primer (E2419K)

<400> SEQUENCE: 15
gtgtcatggc cgtgctgaaa gcctttgtct atgac					35

<210> SEQ ID NO 16
<211> LENGTH: 35
<212> TYPE: DNA
<213> ORGANISM: Artificial Sequence
<220> FEATURE:
<223> OTHER INFORMATION: reverse primer (E2419K)

<400> SEQUENCE: 16
gtcatagaca aaggctttca gcacggccat gacac					35

<210> SEQ ID NO 17
<211> LENGTH: 33
<212> TYPE: DNA
<213> ORGANISM: Artificial Sequence
<220> FEATURE:
<223> OTHER INFORMATION: forward primer (L2427P)

<400> SEQUENCE: 17
gtctatgacc ccttgccgaa ctggaggctg atg          33

<210> SEQ ID NO 18
<211> LENGTH: 33
<212> TYPE: DNA
<213> ORGANISM: Artificial Sequence
<220> FEATURE:
<223> OTHER INFORMATION: reverse primer (L2427P)

<400> SEQUENCE: 18
catcagcctc cagttcggca aggggtcata gac          33

<210> SEQ ID NO 19
<211> LENGTH: 36
<212> TYPE: DNA
<213> ORGANISM: Artificial Sequence
<220> FEATURE:
<223> OTHER INFORMATION: annealing primer

<400> SEQUENCE: 19
aattccaatt gcccgggctt aagatcgata cgcgta       36

<210> SEQ ID NO 20
<211> LENGTH: 36
<212> TYPE: DNA
<213> ORGANISM: Artificial Sequence
<220> FEATURE:
<223> OTHER INFORMATION: annealing primer

<400> SEQUENCE: 20
ccggtacgcg tatcgatctt aagcccgggc aattgg       36

<210> SEQ ID NO 21
<211> LENGTH: 50
<212> TYPE: DNA
<213> ORGANISM: Artificial Sequence
<220> FEATURE:
<223> OTHER INFORMATION: hmTOR-MfeI-flag-F

<400> SEQUENCE: 21
gatcacaatt gtggccacca tggactacaa ggacgacgat gacaagatgc       50

<210> SEQ ID NO 22
<211> LENGTH: 41
<212> TYPE: DNA
<213> ORGANISM: Artificial Sequence
<220> FEATURE:
<223> OTHER INFORMATION: hmTOR-MluI-R

<400> SEQUENCE: 22
tgatcaacgc gtttaccaga aagggcacca gccaatatag c                41